United States Patent
Denenberg et al.

(10) Patent No.: US 6,874,684 B1
(45) Date of Patent: Apr. 5, 2005

(54) AUTOMATED WILL CALL SYSTEM

(75) Inventors: David Denenberg, Easton, PA (US);
Michael Jordan, Alpharetta, GA (US);
Eugene Fellows, Nokomis, FL (US)

(73) Assignee: McKesson Automation Systems Inc., Pittsburgh, PA (US)

(*) Notice: Subject to any disclaimer, the term of this patent is extended or adjusted under 35 U.S.C. 154(b) by 0 days.

(21) Appl. No.: 10/241,171

(22) Filed: Sep. 10, 2002

Related U.S. Application Data

(63) Continuation-in-part of application No. 09/521,763, filed on Mar. 9, 2000, now Pat. No. 6,464,142.
(60) Provisional application No. 60/162,580, filed on Oct. 29, 1999.

(51) Int. Cl.⁷ ............................................. G06F 7/08
(52) U.S. Cl. .................. 235/381; 235/382; 235/385; 902/8; 340/3.1; 340/5.92; 340/568.1
(58) Field of Search .................. 312/215, 326; 340/570, 693.5, 3.1, 5.73, 5.9, 5.92, 568.1, 569; 235/375, 381, 385, 382, 382.5, 462.46, 440, 456; 902/8, 9, 17, 31

(56) References Cited

U.S. PATENT DOCUMENTS

| | | | | |
|---|---|---|---|---|
| 4,633,236 A | * | 12/1986 | Buhl ........................... 340/569 |
| 4,791,411 A | * | 12/1988 | Staar ......................... 340/568.1 |
| 4,814,592 A | | 3/1989 | Bradt et al. .................. 235/381 |
| 4,864,438 A | | 9/1989 | Munro ......................... 360/92 |
| 5,212,649 A | | 5/1993 | Pelletier et al. ............. 700/243 |
| 5,223,829 A | * | 6/1993 | Watabe ...................... 340/5.73 |
| 5,231,272 A | * | 7/1993 | Mardon ....................... 235/382 |
| 5,303,214 A | * | 4/1994 | Kulakowski et al. ........ 235/385 |
| 5,303,844 A | * | 4/1994 | Muehlberger ............... 235/381 |
| 5,313,393 A | * | 5/1994 | Varley et al. ................ 705/28 |
| 5,337,920 A | | 8/1994 | Clausen ......................... 221/5 |
| 5,343,403 A | | 8/1994 | Beidle et al. ............... 700/214 |
| 5,597,995 A | | 1/1997 | Williams et al. ............ 235/375 |
| 5,697,519 A | * | 12/1997 | Wittern et al. ................ 221/76 |
| 5,728,999 A | * | 3/1998 | Teicher ....................... 235/381 |
| 5,905,653 A | * | 5/1999 | Higham et al. ............. 700/244 |
| 5,930,766 A | * | 7/1999 | Gibb ........................... 235/381 |
| 6,010,064 A | * | 1/2000 | Umeda et al. .............. 235/375 |
| 6,189,727 B1 | * | 2/2001 | Shoenfeld ...................... 221/2 |
| 6,433,684 B1 | * | 8/2002 | Lie .............................. 340/569 |
| 6,457,038 B1 | * | 9/2002 | Defosse ...................... 709/200 |
| 6,685,284 B2 | * | 2/2004 | Hara .......................... 340/5.73 |
| 6,715,669 B2 | * | 4/2004 | Hara .......................... 340/5.73 |

FOREIGN PATENT DOCUMENTS

JP            9-202411 A    *  8/1997

* cited by examiner

Primary Examiner—Jared J. Fureman
(74) Attorney, Agent, or Firm—Thorp Reed & Armstrong, LLP

(57) ABSTRACT

A will call system for automating the management of storage and retrieval of items, preferably medical prescriptions. The automated system provides information control of all items in the system. The automated will call monitors the length of time an item remains in the system, and into which location an item is placed. An article sensor provides absolute confirmation that an item has been placed or removed from a designated location in the storage units. The automated will call system uses a controller to permit users to monitor and optimize the storage and retrieval procedures.

39 Claims, 11 Drawing Sheets

AUTOMATED WILL CALL SYSTEM

CROSS REFERENCE TO RELATED APPLICATION

This application is a continuation-in-part of parent application Ser. No. 09/521,763, filed Mar. 9, 2000, now U.S. Pat. No. 6,464,142 which claims priority from provisional application No. 60/162,580, filed Oct. 29, 1999.

FIELD OF THE INVENTION

The present invention relates to will call systems for the storage and retrieval of items. In particular the invention is directed to the improved management of the storage and retrieval of items through the use of an automated will call system.

BACKGROUND OF THE INVENTION

Will call systems and automated storage and retrieval systems are widely used to store, retrieve, and dispense articles. A benefit of such systems is in the speed and efficiency with which items can be stored, retrieved, and dispensed. However, automation has primarily been reserved for the vending machine and central warehouse environments.

Storage and retrieval systems including rotatable storage and retrieval receptacles are known. In such systems, a main platter or shelf is rotated to a window that makes all the storage positions on the shelf available to the window. U.S. Pat. No. 4,814,592 (Bradt et al.), and U.S. Pat. No. 5,212,649 (Pelletier et al.) all show storage systems with circular arrangements of receptacles in the context of systems designed to store specific articles, such as video tapes and magnetic tapes. The systems shown in those patents cannot, however, accommodate articles of different size. U.S. Pat. No. 4,864,438 (Munro) and U.S. Pat. No. 5,343,403 (Beidle et al.) disclose storage and retrieval systems having a stationary storage unit with a moving retrieval system, such as a moving arm. Such a retrieval system takes up a large amount of floor space, which is usually at a premium. Another disadvantage of the systems disclosed in those patents is the length of time necessary to retrieve an article.

U.S. Pat. No. 5,337,920 (Clausen) shows such a device further including a computer system to control the drive assembly to automate the storage and retrieval process. Clausen also provides for the replacement of an item on a storage shelf. However, Clausen does not provide a way to ensure that an item is replaced in the correct location. There is no way to check or supervise the user to keep errors in storage and retrieval to a minimum. The Clausen system may reduce the time for retrieval of an item, but there is no way of checking if items are misplaced.

All of the above cited patents have several drawbacks. First, there is no efficient way to remove articles from the system that remain longer than necessary. In the systems disclosed in those patents, there is no way of determining the age of articles stored. If articles are perishable or otherwise have a value which diminishes the longer the articles remain in the system, there will be waste, loss of potential revenue, and other problems. Second, there is no mechanism to ensure that items are stored and retrieved correctly, i.e., there is no way to minimize operator error. Finally, no system has addressed the handling of controlled articles such as prescription drugs.

To reduce costs, the central fill method of dispensing prescriptions is a growing trend. Demographics indicate that between now and the year 2004, the volume of centrally filled prescriptions will grow from 2.4 billion prescriptions per year to 4.0 billion prescriptions per year, a 40% increase. However, the number of pharmacists will increase by only slightly more than 6% over the same period.

Some systems do exist for batch filling of prescriptions on a volume basis. U.S. Pat. No. 5,208,762 (Charhut et al.), U.S. Pat. No. 5,839,257 (Soderstrom et al.), and U.S. Pat. No. 5,597,995 (Williams et al.) disclose automated systems for prescription filling at a central location, such as for mail order or for batch filling and later delivery to a local pharmacy. Prescriptions are entered into the automated system, automatically filled, packed and labeled, and then delivered to a location for distribution and subsequent patient pickup. Those patents disclose high volume prescription filling systems, but the systems disclosed do not address the problems related to the pick-up of completed prescriptions, where prescriptions could be misplaced, never picked up, or, even worse, dispensed to the wrong patient.

Currently prescriptions enter the pharmacy by several common methods. 1) Hard copy prescriptions are physically brought to the pharmacy by the patient or the patient's representative. The patient either waits for the prescription (or, "script") to be filled, or drops off the script and returns at a later time to retrieve the filled prescription. 2) A doctor or the doctor's representative phones in a new prescription to the local pharmacy and the patient goes to the pharmacy to pick it up after it has been filled. 3) A patient or the patient's representative brings in a previously filled prescription that is renewable or otherwise requests that a renewable prescription be refilled. This request may be made in person or over the phone. For those prescriptions physically brought into the pharmacy, the patient either waits for the prescription to be refilled, or drops off the prescription and returns at a later time to retrieve the refilled prescription.

Almost every retail chain, independent drug store, and outpatient/clinic pharmacy setting currently has some form of manual will call system. The basic functions of a manual will call system are to retrieve a previously filled prescription and hand it to the patient when the patient comes to the pharmacy. There are various physical forms and methods for manual will call. The most common procedure has prescriptions being individually filled and placed into bags, the bags then being filed, alphabetically by last name, in a series of bins or trays located near the point of sale terminals in the pharmacy. This procedure is highly inefficient and prone to error. Disruptions are common to this process and can create a high level of chaos resulting in one or more of the following problems.

Prescriptions can be placed in the wrong bin or tray for pickup. Time is lost looking for a prescription that has been misfiled. When prescriptions are misfiled, the productivity of pharmacy personnel is reduced, the patient faces increased waiting time, and, in extreme cases, the prescription has to be filled a second time (double fill). In high customer demand periods, this can be extremely disruptive and expensive.

The risk of giving a patient the wrong medication is increased in manual will call systems. It is not uncommon for a clerk, particularly during a busy period, to pick up the wrong bag and hand it to the patient without noticing the error. It is not unusual for a patient to also overlook the mistake. The risk of a patient receiving and taking the wrong medication is quite serious and, unfortunately, very real.

Many patients require multiple medications. They may be filled at different times, and placed separately in the bins for pick up. With manual will call systems, there is an increased likelihood that the pharmacy will fail to give the patient all of his prescriptions, since the prescriptions may not always be grouped together in the bins for pick-up. If the patient is not able to pickup all of his prescriptions at once, an additional trip by the patient to the pharmacy is necessary or, even worse, the patient does not realize that there are multiple prescriptions and will not be in compliance with the drug therapy established by the physician.

In addition, most current pharmacy management systems (PMS) do not provide electronic ordering or family grouping of prescriptions. Different members of a household may individually require different medications. With most existing systems, there is no way of assuring that all of the prescriptions for a given household are placed together for pick-up. This can lead to multiple trips to the pharmacy by members of the same household, when all prescriptions could have been collected at one time if they had been grouped together.

From the pharmacy's point of view, unclaimed prescriptions present a problem. An increasing number of prescriptions presented to the pharmacy for dispensing are never picked up by the patient. In most retail pharmacy settings, the pharmacy staff may not necessarily know that a patient has not picked up a prescription and/or does not have the time to call the patient to provide as many reminders as necessary to have the prescription picked up. This lack of a means to remind the patient that a prescription is ready for pickup increases the likelihood that it will never be picked up at all and, therefore, never sold. If unclaimed prescriptions accumulate, they can clog pick up locations and slow down retrieval and increase patient waiting time. They can also represent a loss of revenue to the pharmacy, since medications already dispensed cannot be reused and, if not picked up, constitute waste. Moreover, some medications are perishable, and must be used quickly. If such medications remain unclaimed for too long, they must be discarded and, in some cases, re-dispensed when a patient finally appears to claim them. This leads to increased cost to the pharmacy and, ultimately, to the patient. To clear out unclaimed prescriptions, manual removal or purging of unclaimed prescriptions is required, which is very time consuming and tedious. Most pharmacies do not have the staff or the time to conveniently perform a purge function, thus exacerbating the tendency of the manual will call system to become clogged.

Floor space within a retail chain or independent pharmacy, as well as outpatient and clinic pharmacies, is at a premium. Many of the current will call systems fail to provide a high storage density.

Also, the confidentiality of patients is given a very high priority. Accordingly, the current manually operated bins must be placed far enough away from the sales counter so that the prescription information on the labels cannot be read by other customers. This, of course, runs counter to the need to use less floor space within the pharmacy area, and reduces the efficiency of the will call process. Related confidentiality issues may require that one family member not learn of prescriptions dispensed to other family member. Thus, in some cases there may be a good reason not to group together multiple prescriptions from the same household. Manual will call systems are vulnerable to inadvertently grouping together prescriptions which should remain separate.

The present invention remedies the above disadvantages through automated electronic monitoring of the storage and retrieval of the filled prescriptions.

SUMMARY OF THE INVENTION

The present invention provides an improved method and apparatus for the management of the storage and removal of items, especially, although not necessarily, filled prescriptions. The present invention provides an efficient and accurate will call function by optimizing the storage of items and by electronically tracking the insertion and removal of items.

The automated will call system of the invention tracks the items stored within the system with "absolute confirmation," ensuring that items are inserted and retrieved correctly. The location of stored items is maintained in a memory until the items are removed. Accordingly, there is a reduction in the potential for errors. There is also a reduction in the dispensing of incomplete orders from the will call system by grouping the items according to user-created criteria.

The invention provides high density storage for items by using storage cabinets configured to occupy a minimum of floor space, while providing large storage volume.

The invention also provides for reminders to be automatically sent to patients to pick up items that remain in the will call system for a user-specified time period, permitting the user to use staff time more productively. In addition, an automatic purge process facilitates the removal of items that have remained within the will call system for a user-specified time.

System diagnostic functions provide a way of evaluating the efficiency of the system and user personnel, which helps to lower will call operating costs.

In one embodiment, the present invention is an automated will call system for the management of the storage and retrieval of items, comprising at least one of each of an input source, a storage unit, a user work station, and an article sensor, all in communication with a controller. The controller receives identification data associated with an item to be stored within the system, and stores the identification data in memory. The controller assigns the item a unique storage location within the storage unit. Upon sensing insertion of the item into the unique storage location, by the article sensor, the controller maintains the unique storage location in memory. When the removal of an item from a storage location is sensed by the article sensor, the controller deletes the unique location from memory.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
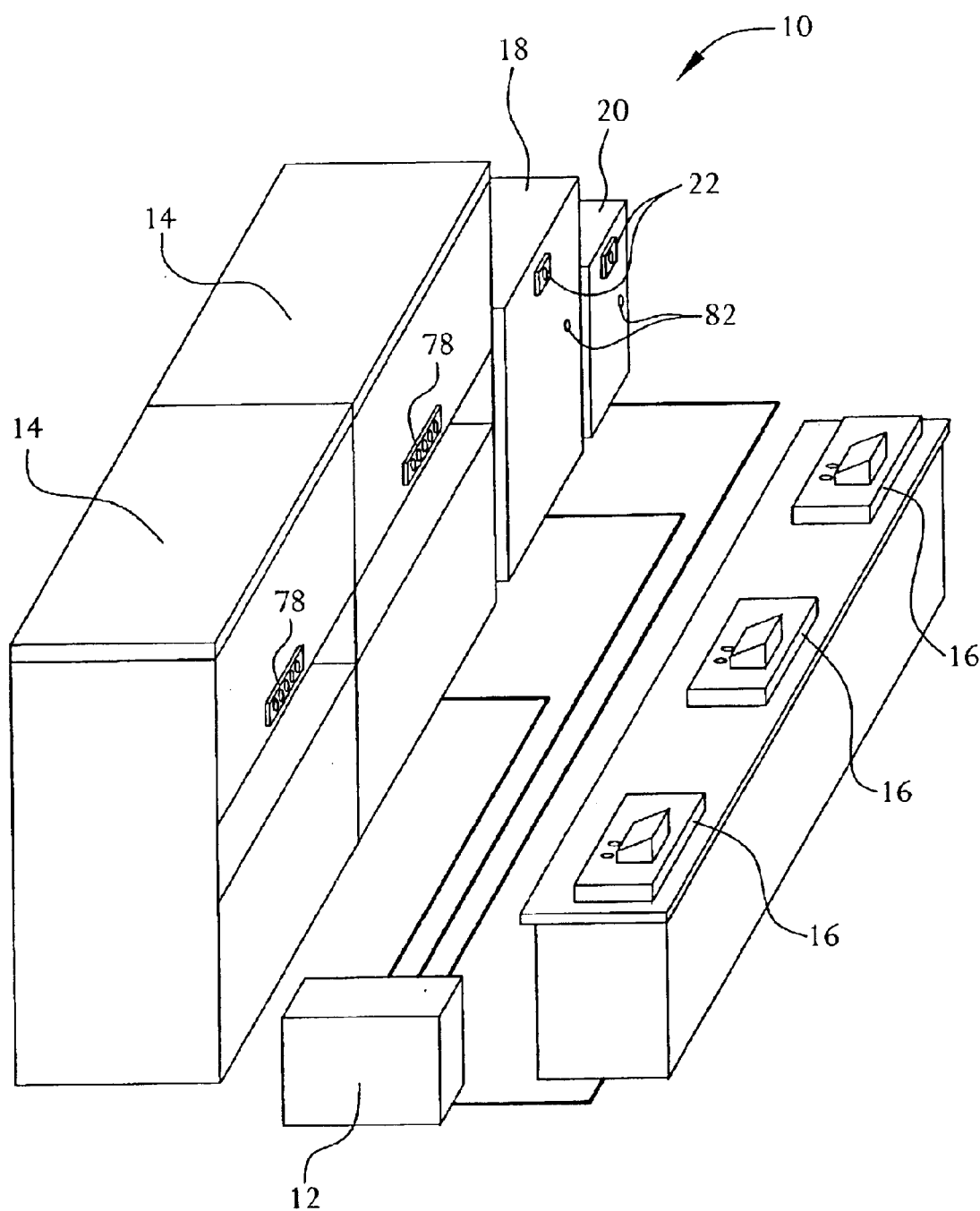
FIG. 1 illustrates a perspective view, in simplified form, of an embodiment of the present invention.

The description contained herein relates to the specific structures of an automated will call system as presently contemplated. This description, however, is intended to be illustrative only and not limiting as to the scope of the present invention. For example, while the invention will be described in the context of storing, retrieving, and dispensing prescriptions, the invention is applicable to storing, retrieving, and dispensing other items as well.

In the drawings, where like numerals indicate like elements, there is shown an automated will call system in accordance with the present invention. The drawings are schematic in that non-essential structures and elements have been omitted.

Figure 2:
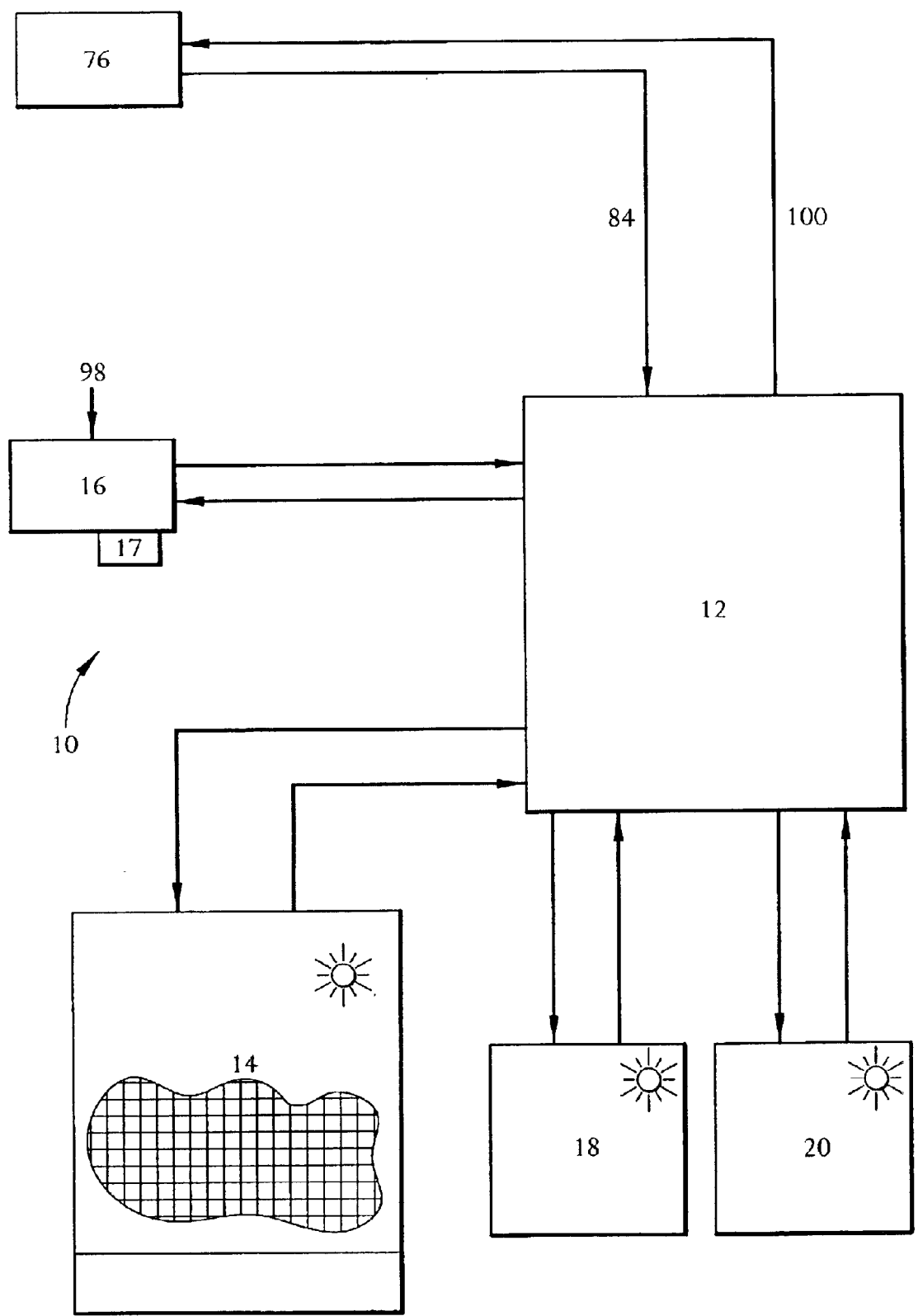
FIG. 2 is a simplified block diagram of the invention of FIG. 1.

As shown in FIGS. 1 and 2, an automated will call system 10 according to the invention includes a controller 12, at least one storage unit 14, at least one user work station 16, and an optional refrigerator 18 and an optional secure storage unit 20. The individual elements of the system are in communication with one another via communication links represented by the solid lines in FIGS. 1 and 2. The lines may be considered to represent hard-wired connections, or optical or wireless connections, as may be desired.

The controller 12 provides all of the command and control functions for the will call system 10, and manages and tracks the movement of items within the system, i.e., their placement into and removal from the system. The controller 12 may be a stand alone device, such as a PC, or may be embedded within the system, such as at a user work station 16 or even within a storage unit 14. The controller 12 includes a memory to store all received information from outside the system (as will be described in more detail below), as well as the locations of all stored items and length of time each item has been in the system.

The storage unit 14 provides a plurality of storage locations for items. At least one opening on the storage unit provides access to the storage locations. The storage locations may be oriented in rows or in columns, and may be moveable to positions providing a user access to the storage locations (as will be described in more detail below).

The user work station 16 provides a site for user and customer interaction with the controller 12, such as the input of item identifying data 98 to identify a particular prescription or prescriptions. User work station 16 may include a card reader 17 associated with it, which can read identifying data 98 from a card swiped through the card reader by a pharmacy clerk or by the customer. The user work station may comprise interactive inputs/outputs such as a monitor and keyboard, scanner, bar code reader, touch screen, voice recognition system, printer, and the like. As seen in FIG. 1, a plurality of user work stations 16 may be provided within the automated will call system, permitting multiple insertions and removals simultaneously at a plurality of storage units 14. They need not be side-by-side as illustrated, but may be remote from one another.

An optional refrigerator 18 for the storage of items requiring refrigeration and an optional secure storage unit 20 for secure storage of valuable or controlled items, such as Drug Enforcement Agency Schedule C2 medications, are in communication with the controller. Associated with the refrigerator and secure unit are a series of lights 22 coded to correspond to the user work stations 16. The refrigerator and secure storage each have at least one user interface button 82, which permits pharmacy personnel to send a signal to the controller which represents the completion of an insertion or removal operation at the designated refrigerator or secure storage unit.

A work flow coordinator, in communication with the controller, comprises a network of indicators for guiding the user. The work flow coordinator may comprise either audible or visible indications, or both for the user. For example, the indications may be in the form of a voice recording directing the user. As seen in FIG. 1, the work flow coordinator preferably comprises incandescent lights 22, 78 disposed on the storage units to guide the user.

The controller 12 receives identification information associated with an item to be stored within the system, and stores that information in memory. The memory may reside within the controller, within a storage unit 14, another PC, the host system 76, or any other system. The identification information may be received in any convenient manner, such as from a pharmacy management system or through direct entry by the user. The direct entry includes any form of input/output found at the user work station 16 or storage unit 14.

Identifying indicia on the exterior of an item is entered into the system. The identifying indicia may be entered in any convenient manner, such as sensing the indicia on the item through use of a scanner at a user work station 16 or at a storage unit 14, or through direct entry by the user. Upon sensing identifying indicia on an item intended for storage within the system, the controller correlates the identification information with the identifying indicia and assigns the item a unique storage location within the storage unit.

Upon user insertion of an item into the unique storage location assigned by the controller, a sensor senses the item insertion and signals the controller. The controller maintains the unique storage location and time of insertion in memory. When it is desired to remove an item from the system, the controller retrieves the unique storage location from memory. Upon sensing the removal of the item from its storage location, the controller deletes the unique location from memory.

All of the embodiments of the invention have at least one storage unit comprising at least one storage location. One embodiment of storage unit employs open shelves, while two other embodiments, one using a conveyor and the other a carousel, have an enclosed cabinet comprising a door or front panel. The conveyor and carousel embodiments have access openings which permit access to a selected number of storage locations. In the case of the conveyor embodiment, the opening permits access to a single row of storage locations, with more than one storage location accessible. In the case of the carousel, the opening permits access to multiple rows of storage locations, but only one storage location per row, i.e., a column.

User interface buttons may be provided on all the storage unit embodiments to enable a pharmacy clerk to confirm the completion of insertion and removal procedures (as will be described in more detail below). This is illustrated schematically in FIG. 2. Alternatively, the user interface buttons may be "virtual" buttons, located on a computer screen or a touch screen.

Figure 3:
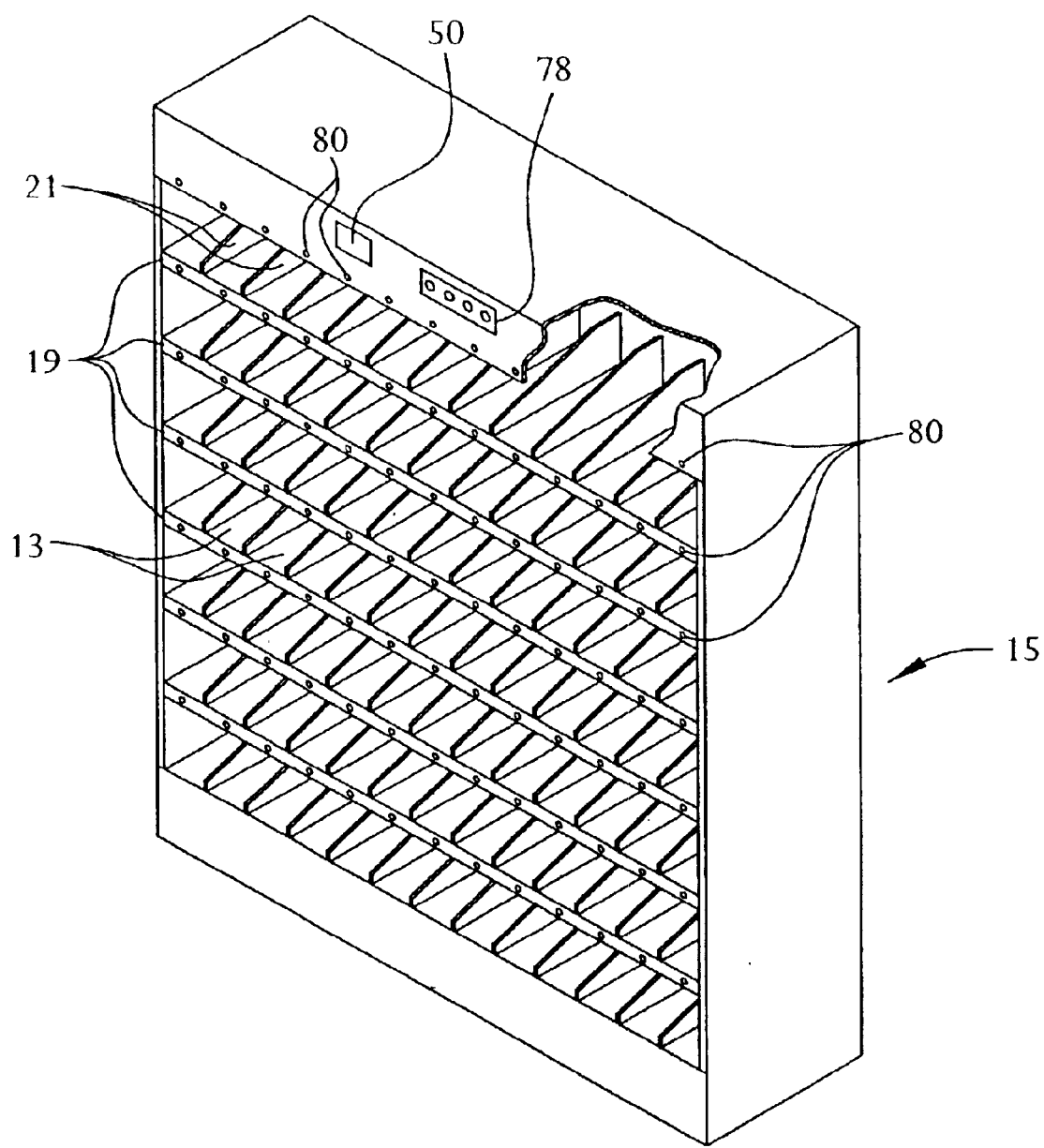
FIG. 3 illustrates one form of a storage unit of the present invention.

One embodiment of storage unit which can be used with the invention shown as in FIG. 3, and is referred to as a "pick-to-light" system. The storage unit is in the form of an open cabinet 15 including a plurality of shelves 19. Each shelf comprises a row of storage locations 13 defined by walls 21. The walls may be either fixed or movable; preferably, but not necessarily, the shelves are fixed in position. A scanner 50 may be attached to the cabinet 15, providing means for pharmacy personnel to input item identifying data into the system.

An article sensor (as will be described in more detail below) may also be attached proximate each storage location, confirming storage or retrieval of an item. The article sensor comprises a light source, a reflector and a photo-detector, arranged so that a light beam emitted from the light source passes through the storage location and reflects off of the reflector back to the photo-detector, adjacent the light source. The reflector may be a reflector strip, reflecting tape, a reflecting coating on a surface, or the like.

A work flow coordinator is provided on the cabinet 15, and may include a row of lights 78 atop the cabinet and an indicator 80 proximate each storage location 13. The indicator 80 provides guidance to the user as to which storage location to use for an insertion or retrieval procedure.

Figure 4:
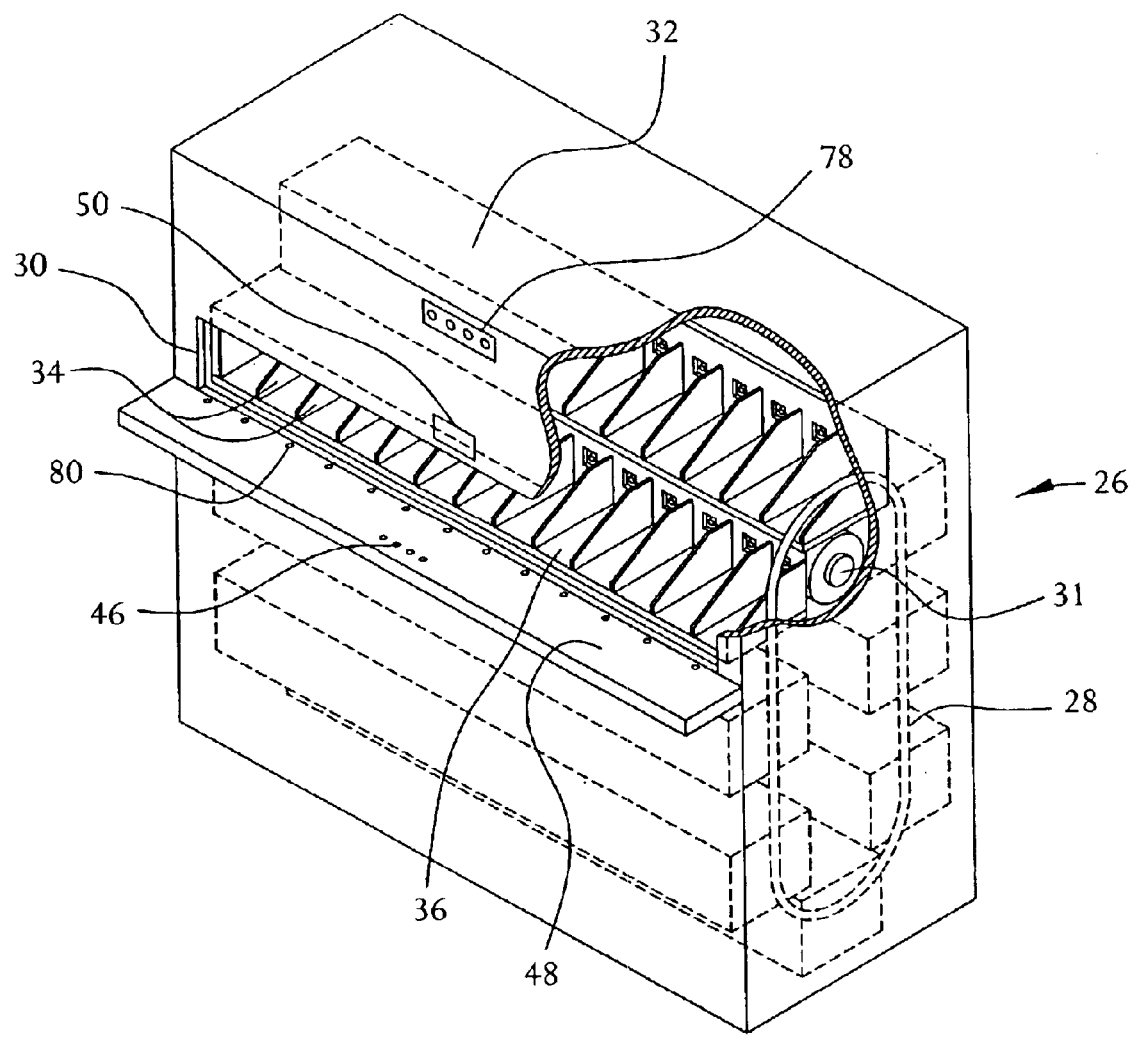
FIG. 4 illustrates another form of a storage unit of the present invention.

Another embodiment of the invention shown in FIG. 4 has a storage unit comprising a cabinet 26 housing a conveyor 28. The conveyor 28 may be disposed in various configurations, but is preferably oriented vertically. The conveyor is rotated by item transport means 31, which may be a drive motor, chain, pulley system, pneumatic device, or the like. The conveyor rotates a plurality of storage locations 36 to a position permitting user access via window 30. The window 30 is sized so as to permit access to a selected number of storage locations at the same time, preferably one row of storage locations 36 at a time.

The conveyor 28 may comprise a plurality of rows 32, each being divided by walls 34 (which may be fixed or movable) which include a plurality of moveable slot members 34. The slot members 34 define the storage locations or slots 36.

Figure 5A:
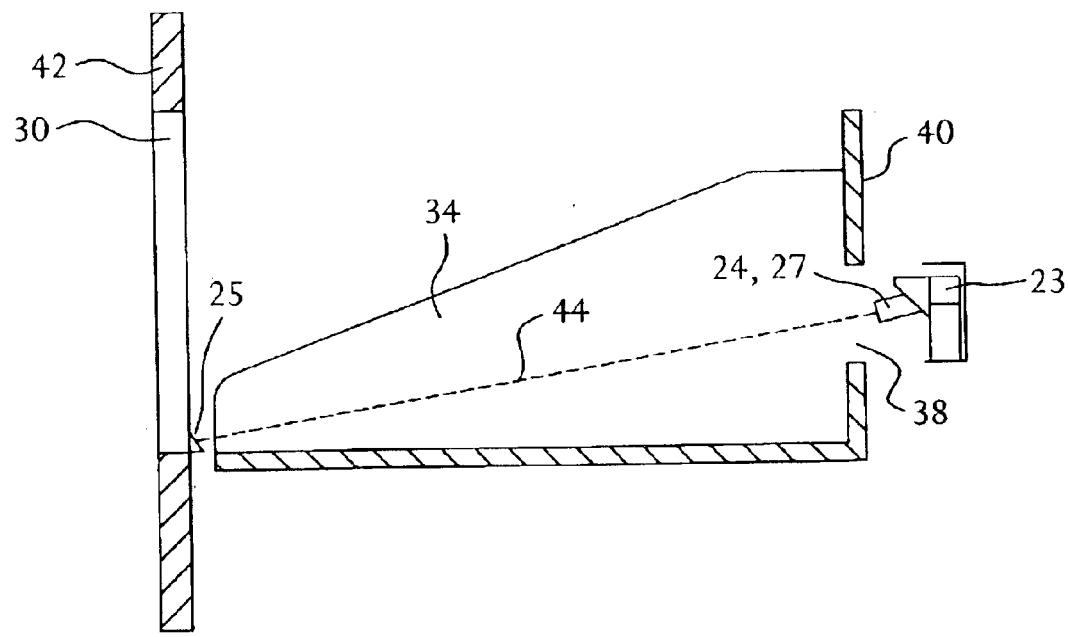
FIG. 5A illustrates a cross-sectional view of a storage location for the storage unit shown in FIG. 4.
Figure 5B:
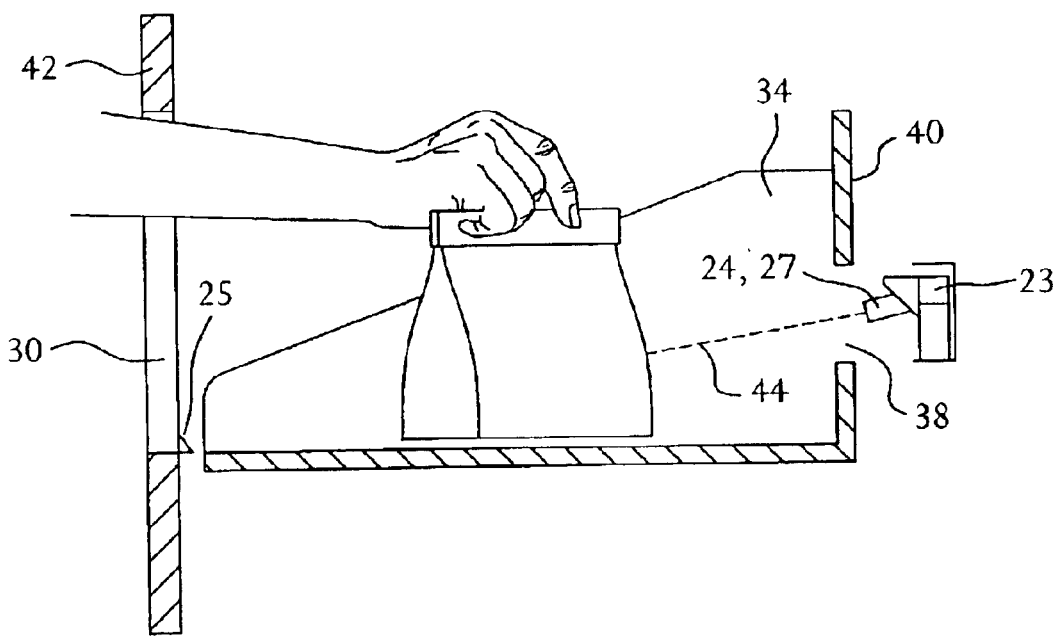
FIG. 5B illustrates a cross-sectional view of a storage location for the storage unit shown in FIG. 4, showing "absolute confirmation" sensing of articles in the storage location.

As shown in FIG. 5A and 5B, an opening 38 is provided on the rear wall 40 of each slot 36. An article sensor 23, comprising a light source 24, is disposed in the interior of the conveyor such that light from the light source 24 passes through the rear wall opening 38 in each slot 36. A reflector 25 is attached to the rear face of the cabinet front panel 42 at the bottom of window 30, generally opposite the light source. A light beam 44 emitted from the light source 24 passes through the storage location and reflects off the reflector 25, back to a photo-detector 27 adjacent the light source 24.

At least one user interface button is provided to generate a signal to represent various functions of the automated will-call system including: procedure complete, next available slot, bulk storage, refrigerator storage, and secure storage. In the illustrated embodiment, a plurality of user interface buttons 46 are shown as being located on the counter 48 of cabinet 26. The user interface buttons may be actual electromechanical devices, or they may be "virtual" buttons, such as on a touch screen, or may be located remote from the storage unit, such as at the user work station 16. More or fewer user interface buttons may be used, as desired.

In addition, a scanner 50 attached to the cabinet 26 provides means for pharmacy personnel to easily input item identifying data into the system. Scanner 50 may scan bar coded data on or associated with an item.

As seen in FIGS. 6, 7, 8A and 8B, and 9, another embodiment of the present invention has a storage unit in the form of an enclosed cabinet 52, having a front panel or door 53, and having at least one carousel 54 contained in the cabinet 52. The door 53 includes at least one opening 55 therethrough, which provides access to storage locations on the carousel. The openings are sized to permit access to a preselected number of slots at the same time, preferably only one slot per carousel at a time. The carousel 54 may vary in size and shape, but preferably the carousel is cylindrical and oriented to rotate about a vertical axis, as in a lazy-Susan design. A drive means 60, preferably disposed on a shelf 62 above the carousel 54, rotates the carousel about its vertical axis. The drive means may be a drive motor, such as a stepper motor, or the like. The carousel may include a plurality of vertically stacked trays 56. Each tray has a plurality of storage locations, preferably in the shape of pie-shaped slots 58 circumferentially spaced and surrounding a central shaft 61. The slots 58 are defined by walls 64, which may be fixed or movable. Each vertically stacked tray 56 may be permitted to rotate independently of the others. The vertical stacking of the trays permits a small footprint while maintaining a high density storage cabinet. For example, a 30" wide by 30" deep cabinet of nominal height would house 144 pie-shaped slots of sufficient size to house normal size prescriptions.

Figure 6:
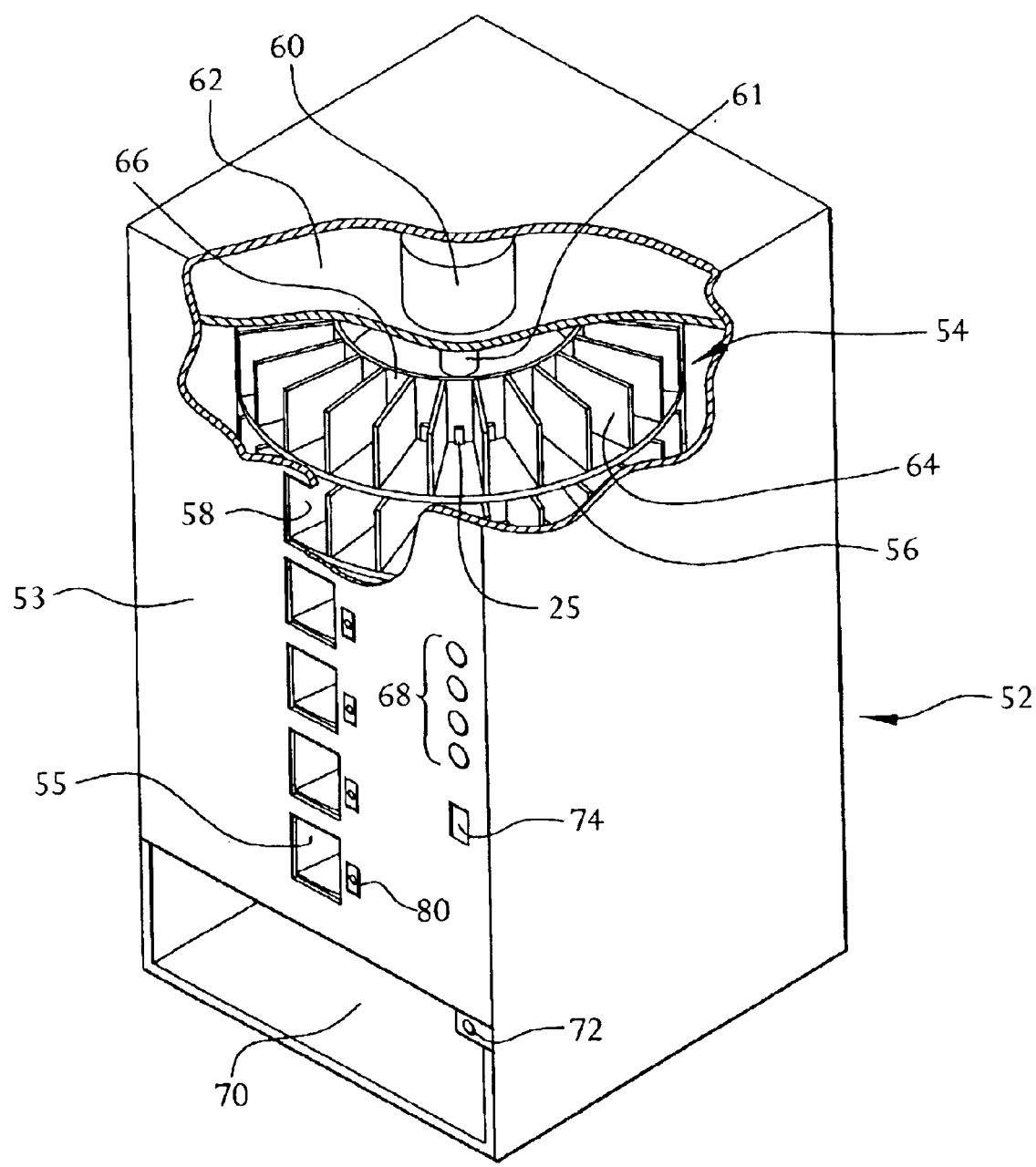
FIG. 6 illustrates a third form of storage unit of the present invention.
Figure 8A:
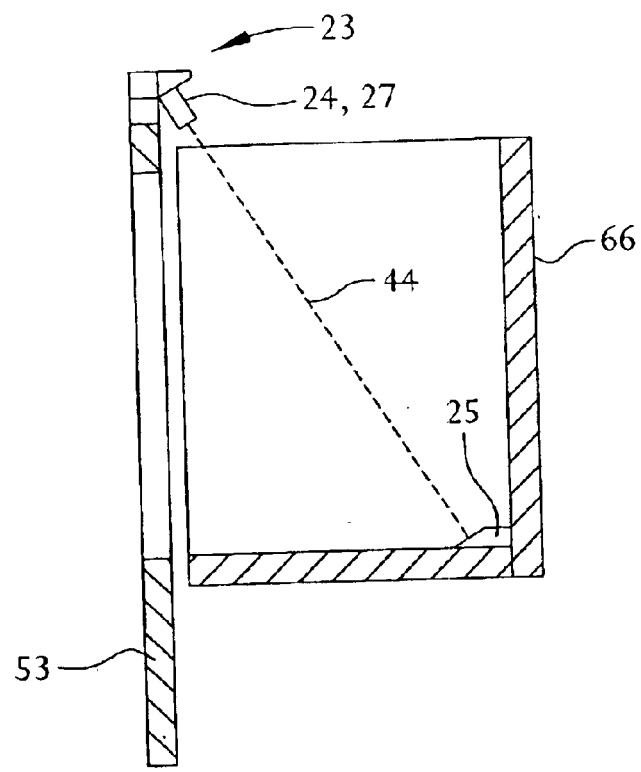
FIGS. 8A and 8B illustrate the "absolute confirmation" sensing of articles in a storage location.
Figure 8B:
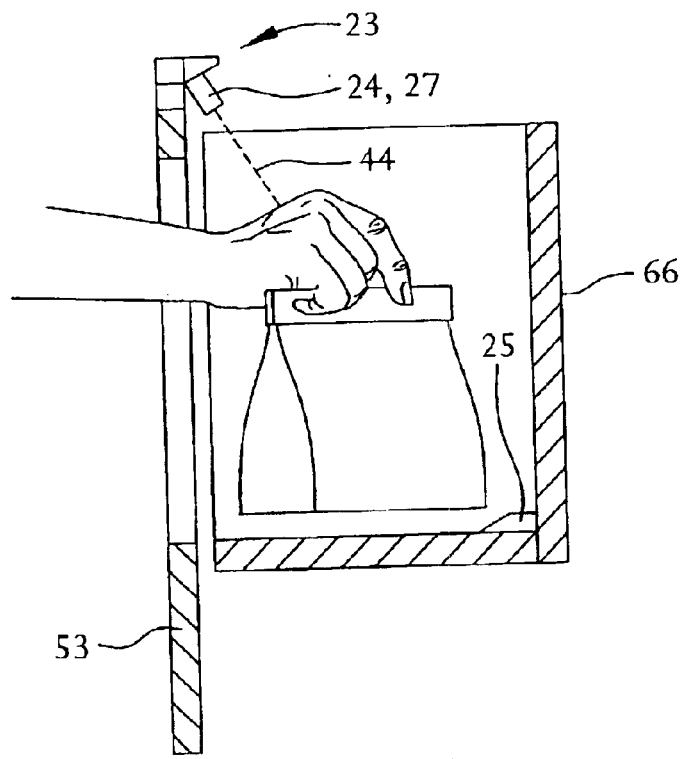

As seen in FIGS. 6, 8A and 8B, each pie-shaped slot 58 includes a reflector 25 at the bottom rear of the slot. A light source 24 is located just above each opening 55, preferably although not necessarily on the inside of the door 53. An article sensor 23, including the light source 24, a reflector 25 and a photo-detector 27, preferably located next to light source 24, transmits signals from the article sensor to the controller, representative of either insertion or removal of an item into or from a storage location. The light source 24, reflector 25, and photo-detector 27 are all arranged and oriented so that a light beam 44 emitted from the light source 24 passes through the storage location, reflects off the reflector 25, and returns to the photo-detector 27 adjacent the light source 24.

FIG. 11 shows another embodiment of the invention, in which the article sensor 123 comprises a light source 124 that differs from those in the embodiment of FIGS. 8A and B. Instead of directing a beam of narrowly focused light 44 as in FIGS. 8A and B, source 124 diffuses light into a pattern 144 that fills the space of the pie-shaped slot 158. In this embodiment, the object 150 acts as a reflector. The reflection of the light back to the photo-detector 127 is accomplished when the object 150, which is reflecting, is introduced into the light-diffused space. The photo-detector 127 detects light reflected from object 150 when the object to be stored is placed in the storage location.

This detection technique is more effective at shorter distances between the light source and the target, and where a larger volume of space may be covered. Consequently, the distance from the light source to the target is generally shorter than in the embodiment of FIGS. 8A and B.

Figure 11A:
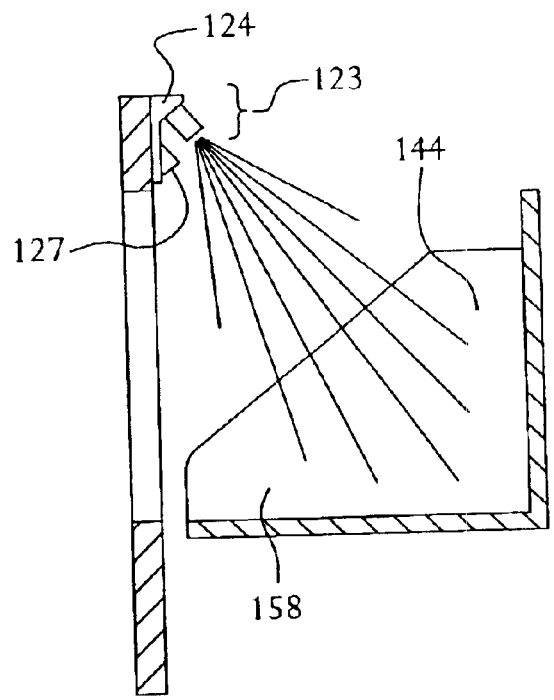
FIG. 11A illustrates another embodiment of the "absolute confirmation" sensing of articles in a storage location, in which the light source emits diffuse light throughout the storage location.
Figure 11B:
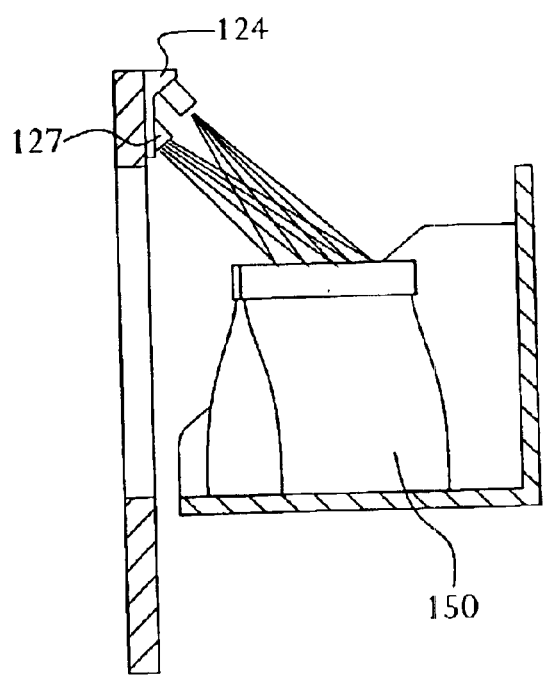
FIG. 11B illustrates that in the embodiment shown in FIG. 11A the reflector is the item itself.

The underlying principle of the automatic confirmation embodiment shown in FIGS. 11A and 11B is the same as that of the embodiment of FIGS. 8A and 8B. In both embodiments, the controller senses the presence or absence of an object in the bin relative to the presence or absence of reflected light. The difference between these embodiments is in the action of the reflecting means. In the embodiment of FIGS. 8A and B, a discrete reflector is always present between the light source and the photo-detector whereas, in the embodiment of FIG. 11, the removable stored object acts as a reflector. In the embodiment of FIGS. 8A and B the controller confirms the presence of an object in the bin by determining an absence of reflected light. That is to say, the stored object blocks the transmission of light to the reflector. When the detector detects no reflected light, the controller interprets that as the presence of a stored object. In the embodiment of FIGS. 11A and 11B, the controller confirms the presence of an object in the bin by determining the presence of reflected light. Put differently, the diffused light from the light source is reflected back to the detector by the object itself, which the controller interprets as the presence of a stored object. If the reflected, diffused light does not exceed a threshold value, the controller interprets this as an absence of an item in the storage location.

With reference again to FIG. 6, a bulk storage area 70 provides a place for the storage of items that do not fit into the slots 58. A light 72 on the bulk storage area prompts the pharmacy personnel to insert or remove items from the bulk storage area, when necessary.

A scanner 74 attached to the cabinet 52, preferably on the door 53, provides means for pharmacy personnel to scan identifying data on an article into the system. As with the previously described embodiment, scanner 74 may be a bar code scanner.

At least one user interface button 68 is located on the cabinet 52, preferably on the door 53. User interface buttons 68 may be provided to represent one or more functions of the system including: procedure done, next available slot, bulk storage, refrigerator, and secure storage, as will be described in more detail below.

The user interface buttons provide a way for a pharmacy clerk to indicate the completion of an insertion or retrieval of an item from a storage location. The user interface buttons represent various functions of the will call system, including: procedure complete (DONE), next available storage location (NEXT), bulk storage (BULK), refrigerator storage (REFRIGERATOR), and secure storage (SECURE). The user interface buttons can be used during both storage and retrieval operations. Additional user interface buttons may be provided to represent as many functions as deemed necessary.

The DONE button provides an indication to the controller 12 that an insertion or retrieval procedure has been completed by the pharmacy clerk. Pressing the DONE button is necessary where an article sensor 23 may not provide indication to the controller 12 that a procedure has been performed. Procedures where an article sensor 23 may not provide indication to the controller 12 include insertion or retrieval of items from bulk storage 70, the refrigerator 18, or secure storage 20. If only one user interface button is provided on a storage unit, it is preferably the DONE button.

The NEXT button provides indication to the controller 12 that the controller designated storage location currently already contains too many items to accommodate an item intended for that location. The user presses the NEXT button to instruct the controller 12 to designate a new storage location for the placement of the intended item.

Depression of the BULK button provides indication to the controller 12 that an item is too large to fit into the designated storage location and that the controller should designate a bulk storage area 70 for storage of the item. Upon insertion of the item into the designated bulk area, the user will press the DONE button, as stated above.

The REFRIGERATOR and SECURE button are used in the same manner as the BULK button. The user presses the intended button, instructing the controller 12 to change the designated storage location to either a refrigerator 18 or secure storage unit 20. Upon insertion of the item into the designated storage location, the user will press the DONE button, as stated above.

The work flow coordinator, in communication with the controller 12, comprises a network of indicators to provide guidance to the user. The work flow coordinator may include audible or visible indications, or both, for the pharmacy personnel to follow. Preferably, the work flow coordinator comprises a network of lights including at least one light 78 attached to each storage unit and at least one light 80 proximate each storage unit opening.

The lights are located to be easily visible to pharmacy personnel. To effectively provide guidance to the user, the lights 78 preferably comprise a row of lights attached proximate the top of the storage unit. The number of lights in the row 78 is preferably equal to the number of user work stations 16 in the system, in addition to at least one error light. The lights may be illuminated steadily or may blink in a predetermined pattern, and the lights may be any shape or color, and may be color coded to correspond to designated user work stations 16.

The controller 12 will activate the work flow coordinator, illuminating the row of lights 78 on the storage unit and the light 80 proximate the designated storage location to guide the user for both insertion and retrieval procedure from a designated storage location. Upon sensing completion of the procedure, the controller 12 will deactivate the work flow coordinator.

Operation of the Automated Will Call System

The operation of the automated will call system is described as being used for management of prescriptions in a pharmacy setting. The users are pharmacy personnel who include pharmacists, technicians, and clerks. However, it should be kept in mind that the invention is not limited to a particular use and is applicable to the storage and retrieval of items in addition to prescriptions.

The prescription dispensing process begins with hard copy prescription requests brought to the pharmacy by the patient or the patient's representative. The patient drops off the script and returns at a later time to retrieve the filled prescription. Alternatively, a doctor or the doctor's representative phones a prescription request into the pharmacy and the patient goes to the pharmacy to pick it up after it has been filled.

As shown in FIG. 2, the system receives patient and prescription identification information 84 to be stored within the automated will call system. The identification information is received at the controller 12. The identification information 84 may be sent via common communication methods from a host system 76, i.e., a pharmacy management system, or entered by pharmacy personnel using interactive input/output units at the user work station 16 or the storage unit 14. The identification information received includes: an order number, patient name, address, phone number, time/date, prescription number, patient identification number, refrigeration required, controlled drug, national drug code (NDC) number, non-grouping flag, or the like. The identification information is stored in memory.

The prescriptions are filled by the pharmacist and placed into bags; the bags are then placed into bins or trays. Alternatively, the prescriptions are filled off-site and shipped to the pharmacy in bins or trays. The filled or partially filled prescriptions, now ready for storage within the automated will call system, are received by pharmacy personnel. Periodically, pharmacy personnel take the bins or trays to the automated will call system to insert the prescriptions for later retrieval for or by customers.

The pharmacy personnel enter the identifying data 98 on the prescription into the automated will call system. The identifying data may be entered at the user work station 16 by manual entry, i.e., keyboard or touch screen, or if the prescriptions are bar-coded, as is preferred, through use of a scanner, preferably through a scanner located at the storage unit 14. The identifying data is correlated, by the controller 12, with other pertinent information such as identification information 84 received from the host system.

In response to receipt of the identifying data, the controller 12 scans for a match with the identification information currently stored in a memory, either its local memory or a remote memory such as at a host computer 76. The controller searches for a match of information such as the patient name, address, phone number, and patient identification number. If a match is found, the controller assigns the same storage location for the prescription as the matched prescriptions currently stored in the system. If no match is found, the controller assigns a unique storage location for the prescription to be placed in the system. The controller 12 preferably designates the closest available storage location for the prescription rather than a predetermined position, thus reducing prescription placement processing time. The designation of the closest available storage location also reduces the required rotation of the item transport means in the conveyor 26 and carousel 52 embodiments.

Prescription grouping may be performed by the system, wherein grouping parameters are designated by the system user, based on any identification information stored in memory. Preferably, prescriptions are grouped by family, using the patient last name and address. Grouping enables the patient to pick up all prescriptions for the patient and other family members at one time.

With grouping, upon receipt of the identifying data, the controller 12 scans the memory for a match of patient last name and address with the identification information of patient prescriptions currently stored in the system. If a match is found, the controller assigns the same storage location for the prescriptions as the matched family prescriptions currently stored in the system.

However, for privacy reasons, a flag may optionally be activated in the automated will call system, preventing automatic grouping for specific patients or scripts. The non-grouping flag may be an audible or visual indication to the pharmacy personnel to not group a specific prescription with others. The indication may emanate from the user work station as an audible signal or a visual signal on a user work station monitor, or a visual indication placed-directly on the prescription. Preferably, the non-grouping flag is included in the identification information 84 received by the controller 12 and stored in memory. During the matching of identifying data with identification information procedure, if a non-grouping flag is found with the matched patient name and address, the controller 12 will automatically assign a unique storage location for the prescription, and grouping will not take place.

Upon controller designation of a storage location, the controller activates the system work flow coordinator. Upon activation of the work flow coordinator, the lights 78 on the designated storage unit illuminate, designating that a storage operation is in progress and guiding pharmacy personnel to the proper storage unit. A light 80 proximate an opening of the storage unit permitting access to the designated storage location illuminates, prompting the pharmacy personnel to insert the prescription into the designated storage location. The pharmacy personnel then inserts the prescription into the storage location proximate the illuminated light 80.

In the conveyor and carousel embodiments, prior to the illumination of light 80, the controller signals the designated storage unit drive means to move the designated storage location to a position that permits user access to the location. In the conveyor embodiment, upon receipt of a signal, the drive means 31 rotates the rows of storage locations 32 on the conveyor until the row containing the designated location is proximate the window opening 30. In the carousel embodiment, upon receipt of a signal the drive means 60, disposed on a shelf 62 above the carousel 54, rotates the carousel of vertically stacked trays to provide access to the designated slot through one of the openings 55.

Once the work flow coordinator prompts the pharmacy personnel to insert the prescription and, if applicable, the drive means has stopped rotating the storage locations, the pharmacy clerk inserts the prescription into the designated storage location.

An article sensor 23, adjacent the designated storage location and in communication with the controller 12, detects the insertion of the prescription into the storage location and sends a signal to the controller confirming the activity. As shown in FIG. 5A, 5B, 8A and 8B, when a prescription is placed within a storage location, the light beam 44 emitted from the light source 24 is blocked, thus preventing the reflection of the light beam off of the reflecting means 25 back to the photo-detector 27. The article sensor 23, in response to the light beam being blocked, sends a signal to the controller representative of a prescription being placed in a storage location. Upon receipt of the signal at the controller that an article has been inserted, the controller deactivates the work flow coordinator, darkening lights 78 and 80, and stores the location of the inserted prescription in the memory. The automated will call system is now ready for another operation.

If pharmacy personnel find a prescription already in the designated storage location, such as when adding a prescription to a group, the pharmacy personnel remove the current prescription from the storage location. The article sensor 23 detects removal of the prescription from the storage location and sends a signal to the controller confirming the activity. The pharmacy clerk then inserts the "new" prescription and the "prior" prescription back into the same designated storage location at the same time. The article sensor 23 detects the insertion of the "new" and "prior" prescriptions. The article sensor sends a signal to the controller representative of the prescriptions being placed into the storage location. Upon receipt of the signal, the controller deactivates the work flow coordinator, and stores the location of the inserted prescriptions in the memory.

If the designated storage location is already full with prescriptions, and the prescription to be inserted will not fit, the pharmacy clerk presses the NEXT user interface button on the storage unit. In response, a signal is sent to the controller 12 instructing the controller that the designated storage location currently has too many prescriptions to accommodate the intended item. The controller scans the memory and designates the closest available storage location for the placement of the prescription. The controller activates the work flow coordinator and item transport means of the designated storage unit, guiding the pharmacy personnel to the new designated storage location. The pharmacy clerk then inserts the prescription into the new designated storage location. Again, upon receipt of a signal from the article sensor 23 indicating insertion, the controller deactivates the work flow coordinator and stores the new designated storage location in the memory.

If the prescription does not fit into a storage location because it is too large, the pharmacy clerk presses the BULK user interface button. In response, a signal is sent to the controller informing the controller that the prescription is too large to fit into the designated storage location and instructing the controller to select a bulk area storage location for the prescription. The controller designates a bulk area location and illuminates a light 72 adjacent the designated bulk area 70, prompting the pharmacy personnel to insert the prescription. The pharmacy clerk then inserts the prescription into the designated bulk storage area. Upon completion of the bulk insertion, the pharmacy clerk presses the DONE user interface button on the storage unit containing the bulk area, confirming completion of the bulk area placement. A signal is sent to the controller in response to pressing the DONE button, instructing the controller to store the designated bulk storage location of the prescription in memory and deactivate the work flow coordinator, including the bulk area light 72.

If the prescription to be stored requires refrigeration, the pharmacy clerk presses the REFRIGERATOR user interface button on the designated storage unit. In response, the controller selects an available refrigerator 18. The controller 12 activates the work flow coordinator on the selected refrigerator 18, illuminating light 22 and directing the pharmacy clerk to insert the prescription into the selected refrigerator. After insertion of the prescription, the pharmacy clerk presses the DONE user interface button 82 on the refrigerator, signaling the controller that the insertion of the refrigeration prescription is complete. In response, the controller 12 deactivates the work flow coordinator, darkening light 22, and stores the refrigeration storage location of the prescription in the memory.

If the prescription to be stored is a valuable or controlled medication, such as Drug Enforcement Agency Schedule C2 medications, and requires secure storage, then the pharmacy personnel presses the SECURE user interface button on the designated storage unit. In response, the controller selects an available secure storage unit 20. The controller 12 activates the work flow coordinator on the secure storage unit, illuminating light 22 and directing the pharmacy clerk to insert the prescription into the selected secure storage. After insertion of the prescription, the pharmacy clerk presses the DONE user interface button 82 on the secure storage unit, signaling the controller that the insertion of the secure prescription is complete. In response, the controller 12 deactivates the work flow coordinator, darkening light 22, and stores the secure storage location of the prescription in the memory.

If the prescription is inserted into the wrong storage location, i.e., the storage location not illuminated by the work flow coordinator, the light beam 44 of the wrong storage location is interrupted, causing a signal to be sent to the controller 12. In response, the controller activates an error signal. This error signal may be audible or visible, or preferably both. Preferably, upon insertion of a prescription into the wrong location, an error light is illuminated and an audible alarm is activated on the storage unit. The error signal remains active until the prescription is removed from the incorrect location. Upon removal of the incorrectly placed prescription, the controller 12 returns the work flow coordinator to the status of instructing the pharmacy personnel to place the prescription in the correct designated storage location. The incorrect storage location may be denoted by the blinking of light 80 proximate said storage location.

When a customer arrives to pick up a prescription, pharmacy personnel initiate the prescription retrieval procedure by entering identifying information about the patient or the prescription to be retrieved. The identifying information may include the patient name, patient identification number, shopper card, retinal scan of the patient, finger print, or the like. The identifying information may be entered by patients themselves or by pharmacy personnel at a user work station 16, using the keyboard, scanner, or card reader 17.

In response to receiving the identifying information, the controller scans the memory for a match with the received information. Upon finding at least one match, the controller may transmit the matched data to the user work station 16 for display to pharmacy personnel. The matched data will be information such as patient name, address, and phone number. Pharmacy personnel may select one of the displayed matches, corresponding to the specific patient and specific prescription(s) for retrieval. The selection of the prescription for retrieval may occur through entry on a keyboard, touch screen, voice recognition, or the like.

If family grouping of prescriptions was done when the prescriptions were inserted into the system, then during retrieval, if there are other prescriptions for the patient or prescriptions for other patients having the same last name, address, phone number, and the like, pharmacy personnel may select any or all of the displayed grouped prescriptions for retrieval by the customer. However, if a non-grouping flag has been activated for a patient's prescription, the controller 12 either displays the non-grouped prescription at the user work station with a non-grouping indication or, preferably does not display the non-grouped prescription at all. The non-group indication may be an audible or a visible indication on the display at the user work station 16. For privacy reasons, the non-grouped prescription may be retrieved only by the individual patient or the patient's pre-designated representative.

Preferably, upon selection of the prescription(s) for retrieval, the controller 12 retrieves the designated location of the selected prescription(s) from the memory and activates the work flow coordinator, and if applicable, the drive means of the designated storage unit. Upon activation of the work flow coordinator, at least one of the lights 78 on the designated storage unit illuminates, designating a prescription retrieval activity in progress and guiding pharmacy personnel to the proper storage unit. Preferably, one of the lights 78, color coded to the user work station 16 where the retrieval was initiated, is illuminated. Also, a light 80 proximate the opening of the storage unit permitting access to the designated storage location illuminates, prompting the pharmacy personnel to remove the prescription from that designated storage location. The pharmacy clerk then removes the prescription from the storage location proximate the illuminated light 80.

In the conveyor and carousel embodiments, prior to the illumination of light 80, the controller signals the designated storage unit drive means to move the designated storage location to a position which permits user access to the storage location. In the conveyor embodiment, upon receipt of a signal, the drive means 31 rotates the rows of storage locations 32 on the conveyor until the row containing the designated storage location is proximate the window opening 30. In the carousel embodiment of the invention, upon receipt of a signal the drive means 60 rotates the carousel of vertically stacked trays until access to the designated storage slot is permitted, through one of the openings 55.

Once the drive means has stopped rotating the storage locations and the work flow coordinator prompts the pharmacy personnel to retrieve the prescription, the pharmacy clerk removes the prescription from the designated storage location.

The article sensor 23, adjacent the designated storage location and in communication with the controller 12, detects the removal of the prescription from the storage location and sends a signal to the controller confirming the removal. As shown in FIG. 5A, 5B, 8A and 8B, when a prescription is removed from a storage location, the light beam 44 emitted from the light source 24 is no longer blocked by the prescription, and is permitted to reflect off of the reflecting means 25 back to the photo-detector 27. The article sensor 23, in response to the light beam reflecting back to the photo-detector, sends a signal to the controller representative of a prescription being removed from a storage location. Upon receipt of the signal that the prescription has been removed, the controller deactivates the work flow coordinator, darkening lights 78 and 80, and deletes the location of the retrieved prescription from the memory. The automated will call system is now ready for another activity.

If there are multiple prescriptions in multiple storage locations to be retrieved for the customer, the controller identifies the current storage location(s) permitting user access therein, and then activates the drive means to rotate the storage locations to permit access to the closest designated storage location containing the multiple prescriptions to be retrieved. Once the article sensor 23 detects removal of the first prescription from the storage location, a signal is sent to the controller confirming the first retrieval. The controller then activates the work flow coordinator, and if applicable, the drive means, to provide access to the designated storage location of the second prescription to be retrieved. This process is repeated until all selected prescriptions have been retrieved. Upon receipt of the signal representative of the last retrieval, the controller deactivates the work flow coordinator, and deletes the locations of the retrieved prescriptions from the memory. If pharmacy personnel find more than one prescription in the designated storage location, the pharmacy clerk removes all prescriptions from the storage location.

If the prescription to be retrieved was stored in a bulk area, the controller activates the work flow coordinator, illuminating light 72 on the appropriate bulk area 70, directing the pharmacy clerk to retrieve the prescription from the designated bulk storage area. Upon removing the prescription from the bulk storage area, the pharmacy clerk presses the DONE user interface button on the bulk storage unit, confirming completion of the retrieval. A signal is sent to the controller in response to depression of the DONE button, instructing the controller to delete the bulk storage location from the memory and deactivate the work flow coordinator, including the bulk area light 72.

If the prescription was stored in a refrigerator, the controller activates the work flow coordinator on the appropriate refrigerator 18, illuminating light 22 and directing the pharmacy clerk to remove the prescription from the refrigerator. The clerk then removes the prescription, and presses the DONE user interface button 82 on the refrigerator, signaling the controller that removal of the refrigeration prescription is complete. In response, the controller 12 deactivates the work flow coordinator, darkening light 22, and deletes the refrigeration storage location from the memory.

If the prescription is a valuable or controlled medication that was stored in secure storage, the controller activates the work flow coordinator on the appropriate secure storage unit, illuminating light 22, directing the pharmacy clerk to remove the prescription from the secure storage unit. The clerk then removes the prescription, and presses the DONE user interface button 82 on the secure storage unit, signaling the controller that the retrieval of the secure prescription is complete. In response, the controller 12 deactivates the work flow coordinator, darkening light 22, and deletes the secure storage location from the memory.

In the multiple prescription retrieval situation, pharmacy personnel may program the controller to prioritize access to the retrieval locations. Preferably, retrieval of prescriptions from the refrigerator 18 and secure storage unit 20 are initiated by the controller 12 before retrievals from the storage units 14, i.e., pick-to-light shelf, conveyor, and carousel. This is to ensure that pharmacy personnel do not forget to retrieve those prescriptions.

The controller may prioritize other will call functions. For example, retrieval of a prescription preferably will take precedence over the storage of a prescription. Thus, if a prescription needs to be retrieved while others are being inserted, the system will permit insertions already in process to be completed, but will place further insertions on hold until the retrieval operation has been completed.

If a prescription is removed from the wrong storage location, i.e., the storage location not illuminated by the work flow coordinator, the light beam 44 in the wrong storage location will reflect off the reflecting means 25 to the photo-detector 27, causing a signal to be sent to the controller 12. In response to the signal, the controller activates an error signal. This error signal may be audible or visual, or both. For example, upon removal of a prescription from the wrong location, an error light is illuminated and an audible alarm is activated on the storage unit. The error signal remains active until the improperly removed prescription is replaced in its correct location. Upon replacement of the incorrectly removed prescription, the controller 12 returns the work flow coordinator to the status of directing the pharmacy clerk to retrieve the prescription from the correct designated storage location. The incorrect storage location may be denoted by the blinking of light 80 proximate said storage location.

Additional System Functionality

The present invention may also provide capabilities to permit modification of the performance of the system, and monitoring of system functions and the performance of pharmacy personnel. The capabilities may include reminders to patients, purging of old prescriptions, and system diagnostics.

To minimize the number of unclaimed prescriptions, the system may automatically communicate with patients to remind them that their prescription is ready for pick-up. Since many prescriptions are called in and processed through a host system, such as an Interactive Voice Response (IVR) system, the present invention tracks the date and time a prescription is entered into the system, and stored within a storage unit.

As stated earlier, prescriptions enter the system by pharmacy personnel entering identifying data 98 related to the prescription. The identifying data is entered at the user work station 16 by manual entry, i.e., keyboard or touch screen, or through use of a scanner. The controller stores the prescription entry time in memory. After prescriptions have remained in the system a predetermined period of time, the system may automatically call the patient to remind the patient that the prescription is ready for pick-up. Preferably, the controller 12 automatically sends electronic reminder signals 100 to the host IVR unit 76, which in turn, places an automated call to the patient to provide a reminder that the prescription is ready for pick-up.

Pharmacy personnel may specify the time period prescriptions must remain in the system before a reminder signal is sent, by entering the time period at a user work station 16 or other computer terminal in communication with the system. The reminder signal 100 parameters may be chosen as that reminders are sent after a preselected length of time, repeatedly sent at a user specified time interval, or sent a user specified number of times.

Alternatively, pharmacy personnel may prompt the controller to print out a listing of the patients, and their phone numbers, who have prescriptions remaining in the system longer than the specified period, allowing pharmacy personnel to call personally and remind the patients to pick up their prescriptions.

A purge process may be performed to remove prescriptions that have remained unclaimed in the system. The purge process, initiated by pharmacy personnel at the user work station, prompts the controller 12 to identify all prescriptions that have been in the system longer than a user specified time period.

In response to initiation of the purge process, the controller 12 scans its memory and retrieves the storage location of all prescriptions that have been in the system for longer than the time period specified by the pharmacy personnel. The controller then signals the system to guide the pharmacy personnel to the storage location closest to a storage unit opening with a prescription to be removed.

The controller activates the work flow coordinator, illuminating lights 78 on the designated storage unit and illuminating light 80 proximate the designated storage opening. Prior to illumination of the lights 80, if applicable, the controller signals the designated storage unit item transport means to move the designated storage location to a position that permits user access to said storage location. Pharmacy personnel remove the prescription in response to the system prompts. Once the unclaimed prescription is removed, the system immediately deactivates the currently activated work flow coordinator, and then activates the work flow coordinator and item transport means of the storage unit containing the next prescription to be purged. The system repeats this process in a continuous manner until all unclaimed prescriptions designated to be purged have been removed from the system. Prescriptions removed from the bulk storage, refrigerator, or secure storage are preferably scanned by a scanner, retrieving identifying information and sending it to the controller 12 for deletion of the prescription location from memory.

The purge process is preferably performed periodically when prescription insertion and retrieval operations are least active, e.g., when the pharmacy is closed.

System self-test diagnostics may be initiated by pharmacy personnel, causing the controller to perform a series of routines to test the system functions and hardware. The tests may prompt the user to perform an action, e.g., ask the user to provide visual confirmation that all lights in the work flow coordinator illuminate. As another, example, a re-synchronization process permits pharmacy personnel to verify that there is a prescription in a slot that is supposed to have a prescription and verify that there is no prescription in a slot that is not supposed to have a prescription. The re-synchronization is typically performed when will call activity is at its lowest.

Preferably, when prompted by the user, the system may print out a report of activity in the system (storage and retrievals). Using the print out, pharmacy personnel may manually manipulate the storage units to inspect the storage locations and verify that prescriptions are in their proper location. Alternatively, the printouts may be automatically printed at user selected time intervals so that in the event of an emergency, such as if power is lost, pharmacy personnel may use the printouts to manually operate the will call system. For example, the door 53 of a cabinet 52 containing the carousel 54 may be manually opened and the carousel manually rotated, permitting access to desired storage locations, thus allowing the will call process to continue in the absence of electrical power.

Figure 7:
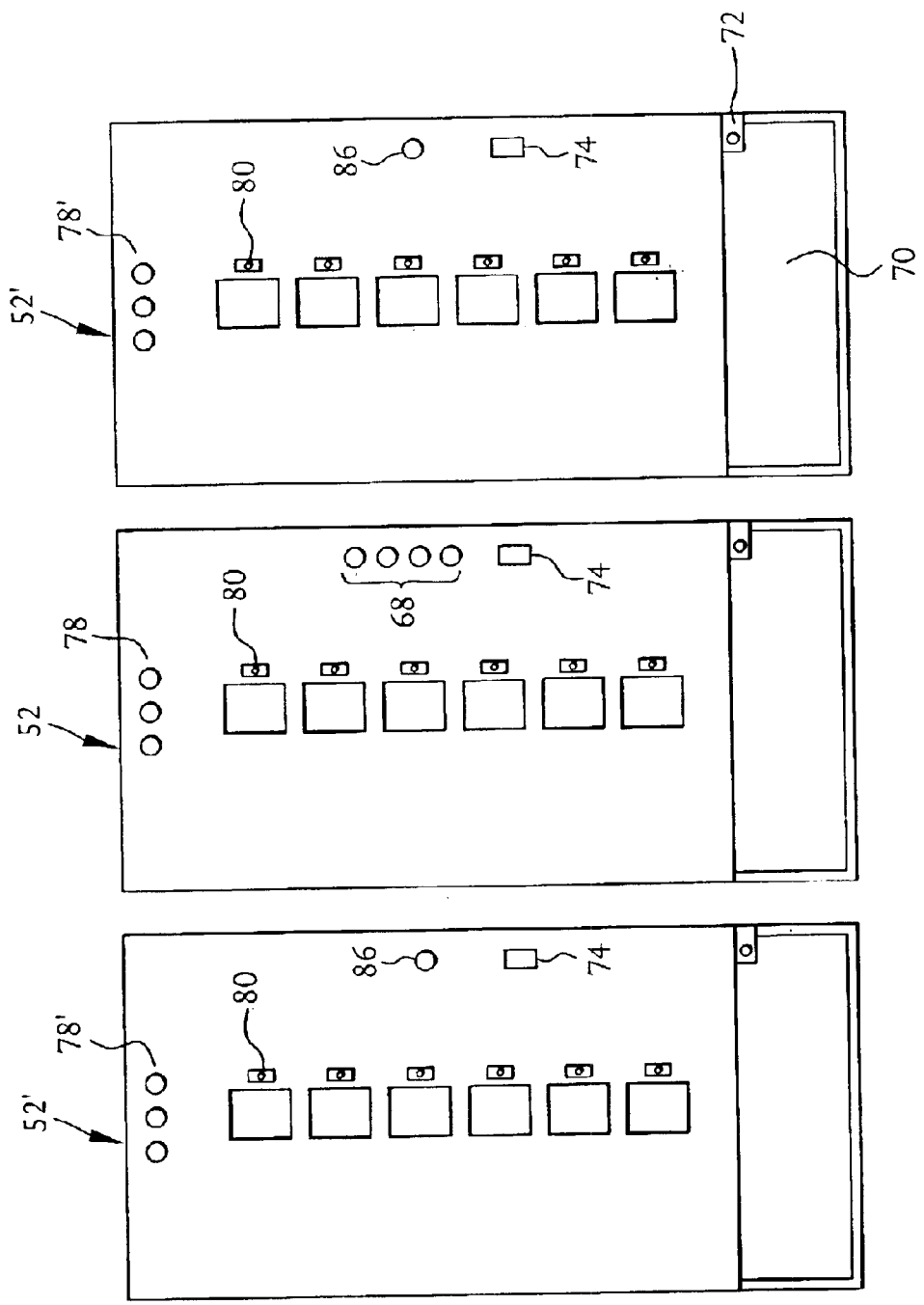
FIG. 7 illustrates an embodiment of the present invention in which plural storage units as in shown in FIG. 6 are grouped together.

As shown in FIG. 7, the automated will call system may include several storage cabinets. In such a configuration, one cabinet 52 is the "master" cabinet and the remaining cabinets are "auxiliaries" 52'. The master cabinet and auxiliary cabinets are in communication with the controller 12 via communication links. These links may be hard-wired connections, or optical or wireless connections, as desired.

The master cabinet 52 comprises a plurality of user interfaces buttons 68, as previously described. The auxiliary cabinets 52' are the same as the master cabinet, with the exception of having a single user interface button 86, preferably a DONE button. The DONE button provides indication to the controller 12 that an insertion or retrieval procedure has been completed by pharmacy personnel at that cabinet.

As stated above, pressing the DONE button is necessary where an article sensor 23 may not provide indication to the controller 12 that a procedure has been performed. Procedures where an article sensor 23 may not provide indication to the controller 12 include insertion or retrieval of items from bulk storage 70, the refrigerator 18, or secure storage 20. For the insertion into and retrieval from these storage locations, pharmacy personnel utilize the user interface buttons on the master storage cabinet 52, and only use the DONE button on the auxiliary cabinet 52' when a prescription is inserted in or retrieved from that auxiliary cabinet bulk storage area.

All embodiments of the storage cabinets may include at least one high density storage location having a larger volume than the storage locations described above. Preferably, the high density slots would reside within the carousel storage cabinet 52, wherein an article sensor 23 senses that at least one prescription is inserted into or removed from a high density slot. However, several prescriptions may be in the single slot. The high density slots are for high volume prescription storage, wherein the pharmacy personnel would know that a prescription is one of many prescriptions within a large slot/bin. For retrieval of a prescription from a high density storage slot, pharmacy personnel interact with the controller 12 in the same manner as in a typical retrieval. In response, the controller communicates with the work flow coordinator and drive means to guide the pharmacy personnel to the proper high density slot containing the prescription to be retrieved. Pharmacy personnel then sort through a relatively small number of prescriptions in the slot to locate the correct prescription. The high density storage configuration significantly decreases the retrieval time since pharmacy personnel are directed to a relatively small number of prescriptions out of a vast number of prescriptions stored in a single cabinet.

Figure 9:
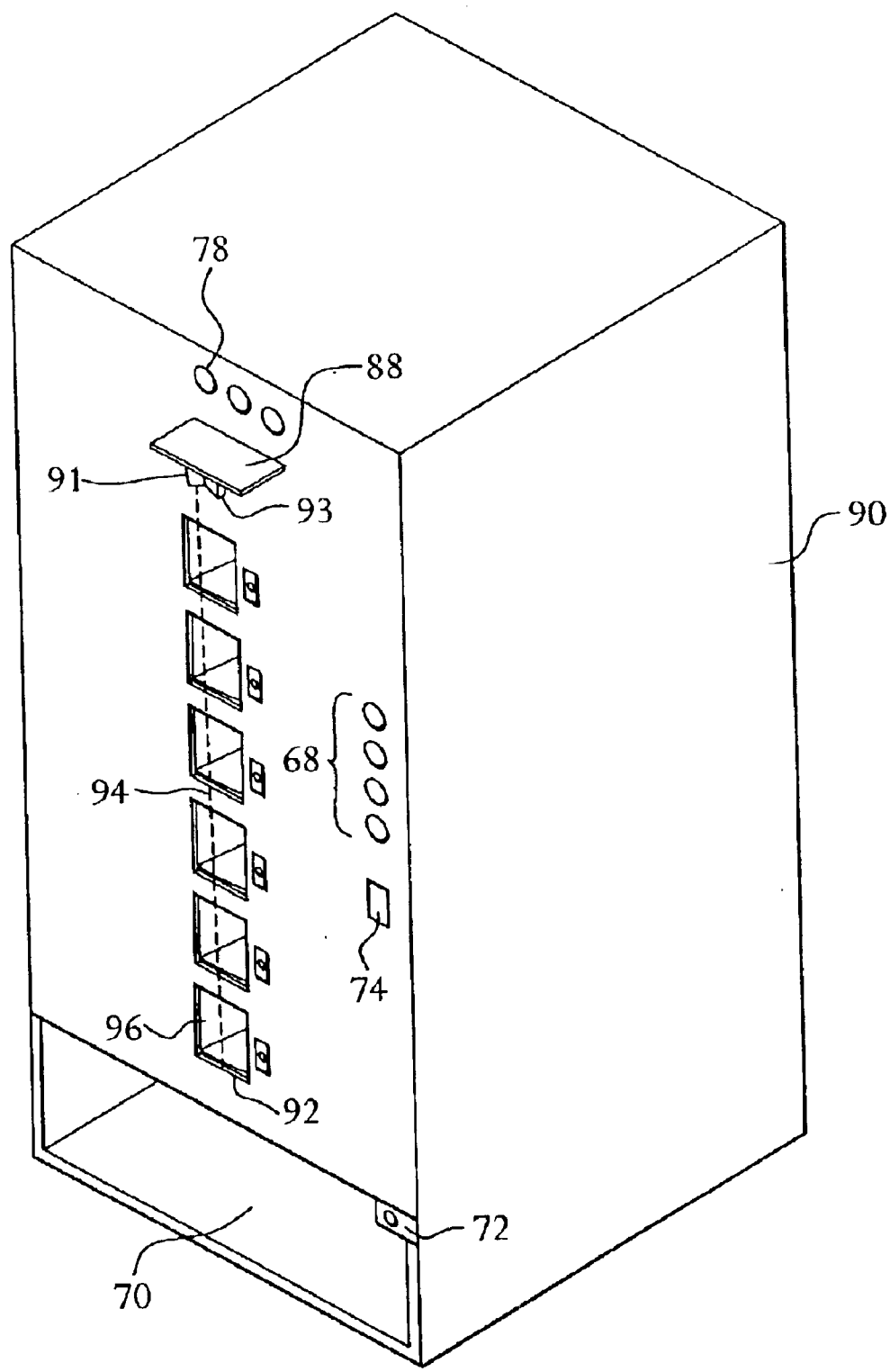
FIG. 9 illustrates a safety sensor for the storage unit shown in FIG. 6.

As shown in FIG. 9, a safety sensor 88 may be attached to the cabinet 90, including a light source 91, a reflecting surface 92, and at least one photo-detector 93 adjacent the light source. The light source 91 is oriented so as to direct a light beam 94 to strike a reflecting surface 92 on the lower edge of an opening 96 on the cabinet 90, thereby providing a "light curtain." Preferably, the light beam 94 emitted from light source 91 is oriented to strike a reflecting surface 92 located on the lower edge of the lowermost opening 96 in the cabinet.

There may be one light beam for each opening 96 in the cabinet 90. For example, each light beam may be individually oriented to strike a reflecting surface 92 located on the lower edge of each opening in the cabinet.

The "light curtain" operates in the same manner as the article sensors 23. When an object, e.g., a hand, interrupts the light beam 94, preventing the light beam from reflecting off of the reflecting surface 92 and being reflected to the photo-detector 93, a signal is sent to the drive means to stop the movement of the conveyor or carousel until the light beam is restored. Accordingly, injury to pharmacy personnel and damage to the prescription is avoided.

Via the IVR and PMS, prescriptions can be filled in a central location (central fill), transported to the pharmacy through any suitable logistical method, and then placed into a will call system, according to the invention. "Predictive refills," wherein pharmacies send patients refills to prescriptions prior to the end of a current prescription expiring or prior to the patient requesting a refill, would benefit from the automated will call system of the invention. To that end, another embodiment of the carousel cabinet 52 comprises removable vertically stacked trays of slots 58. Each slot is preferably pie-shaped and circumferentially offset. Each tray of slots comprises two semi-circular portions, each portion forming a tote 102.

The tote 102 is filled with completed prescriptions at the central fill location and transported to the pharmacy, where the storage cabinet 52 resides. The prescription identifying information, as well as the slot location of each filled prescription transported in the tote 102, is stored and sent to the pharmacy to be entered into the system. The prescription identifying information and slot location of the transported prescriptions may be entered into the controller memory by electronic transmission, such as via modem, or the prescription identifying information may be stored in a memory device and shipped with the tote 102 in the form of a bar code or read/write tag 104 disposed on the tote, a separate disk, or the like.

As the filled prescriptions are inserted into the totes 102 at the central fill location, the identifying data 98 on each prescription is entered into a host system, along with the slot location 58 into which the prescription was inserted. Preferably, the identifying data on the prescription is entered through the use of a scanner. Once the tote 102 is filled, the identifying data is captured and stored on the memory device 104, preferably on the tote 102. The tote is then shipped to the pharmacy.

Figure 10:
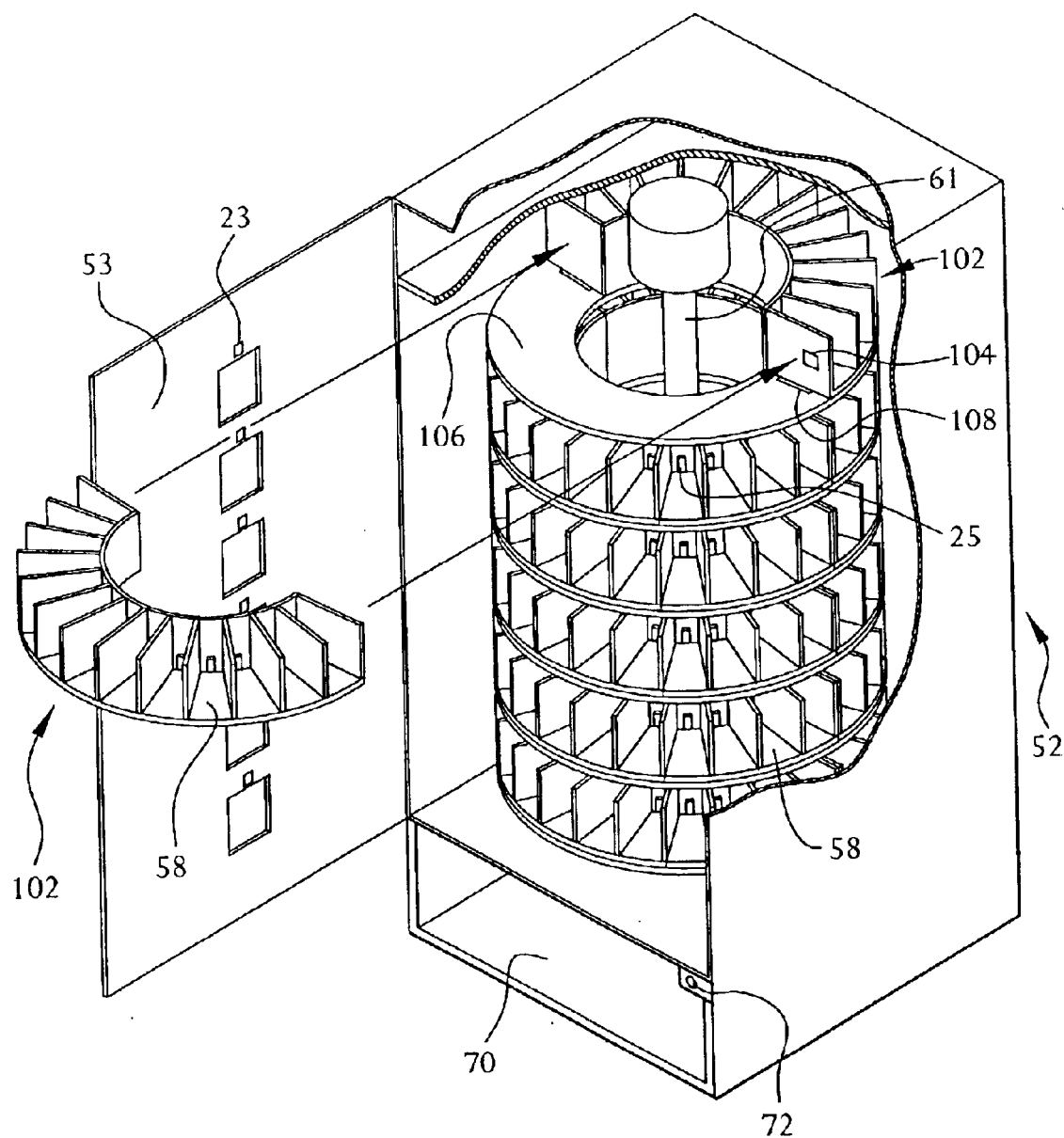
FIG. 10 illustrates a tote for holding articles, which can be used with the storage unit shown in FIG. 6.

Upon arrival at the pharmacy, pharmacy personnel locate an available storage cabinet 52 to accommodate the tote. The memory device 104, preferably disposed on the tote, is read by a scanner 74, which sends to the controller memory all the identifying data and slot locations of the prescriptions within the tote. Pharmacy personnel then insert the tote 102 onto the available shelf 106 of the vertically stacked rows of slots 58, as seen in FIG. 10. The semi-circular tote rests on top of the shelf 106 and is releasably attached to the shelf by attachment means 108. The carousel may be manually rotated to a position permitting insertion of the tote. Two semi-circular totes 102 disposed adjacent each other on a shelf form a continuous circle of slots circumferentially disposed about a central shaft 61.

The totes permit the transportation of central fill prescriptions to a pharmacy in batch form, and eliminate need for the insertion of individual prescriptions into the automated will call system by pharmacy personnel.

It will be appreciated that the invention permits a self-service unit including automatic payment capabilities, similar to an automated teller machine (ATM) or an automated card reader. The self-service interface may include a touch screen and a finger print reader or retinal scan unit to verify the identity of patients, for control of the prescription dispensing. The patient can subsequently retrieve a prescription without relying on pharmacy personnel to do so. To ensure that the patient is given the correct prescription, the self-service system may, although it need not, be equipped with a single door or with individually secure doors which open and close automatically and provide patient access to only the appropriate storage location or locations.

The automated will call system may be connected to "point of sale" terminals or other host systems within a retail pharmacy setting. The connection may include automated signature pads, ATM capabilities, and a cash register, ensuring prompt payment and verification for the retrieved prescriptions.

Finally, speed and accuracy of service are critical in the delivery of prescriptions in the retail pharmacy or outpatient/ clinical pharmacy setting. Retrieval of the correct prescription as quickly as possible, and satisfaction of the patient is the goal of this system. Testing has shown that the embodiment of the invention using the carousel transport system will present the correct prescription for retrieval in 4 seconds or less.

Modification, change and substitution are intended in the foregoing disclosure. In some instances, some features of the invention will be employed without a corresponding use of other features. Accordingly, it is appropriate that the claims be construed broadly and in a manner consistent with the spirit and scope of the invention herein.

The present invention may be embodied in other specific forms without departing from the spirit or essential attributes thereof and, accordingly, reference should be made to the appended claims, rather than to the foregoing specification, as indicating the scope of the invention.

What is claimed is:

1. An automated will call system comprising:
    a) an input source for providing identification information;
    b) a controller for management of storage and removal of items within the automated will call system, the controller receiving identification information from the input source and in response thereto generating a signal representative of a location of an associated item for tracking said item within the will call system;
    c) a plurality of cabinets for the storage of items, each cabinet comprising an interface with the controller, a plurality of storage locations, and at least one interface button;
    d) at least one article sensor for each cabinet comprising a light source and a photo-detector, the light source emitting diffused light throughout an interior of at least one storage location and the photo-detector detecting the presence of the diffused light, each article sensor being in communication with the controller for monitoring the diffused light and providing absolute confirmation of insertion of an item into or removal of an item from a storage location in response to diffused light detected by the photo-detector; and e) a user work station comprising an interface with the controller.

2. An automated will call system as claimed in claim 1, wherein the input source is any one of the group comprising: a bar code reader, user work station, and host computer system.

3. An automated will call system as claimed in claim 1, wherein the signal activates a visible indicator.

4. An automated will call system as claimed in claim 3, wherein the visible indicator comprises at least one indicator light.

5. An automated will call system as claimed in claim 4, wherein the automated will call system further comprises:

a refrigerator comprising at least one indicator light and a controller interface button; and a secure storage unit comprising locking means, at least one indicator light and a controller interface button.

6. An automated will call system as claimed in claim 1, wherein the signal activates an audible indicator.

7. An automated will call system as claimed in claim 1, wherein each cabinet further includes a drive means.

8. An automated will call system as claimed in claim 7, wherein the plurality of storage locations for each cabinet are located on a carousel.

9. An automated will call system as claimed in claim 8, wherein each cabinet further comprises a front panel having an opening therethrough dimensioned to permit access to a selected number of storage locations at one time.

10. An automated will call system as claimed in claim 9, wherein each front panel has a plurality of openings therethrough.

11. An automated will call system as claimed in claim 9, wherein:

each front panel comprises a front face and a rear face; and each photo-detector is attached to the rear face of each front panel.

12. An automated will call system as claimed in claim 8, wherein each carousel comprises a row of storage locations.

13. An automated will call system as claimed in claim 12, wherein each row of storage locations are circumferentially offset about a vertical shaft.

14. An automated will call system as claimed in claim 13, wherein each carousel further comprises a plurality of vertically stacked rows of storage locations.

15. An automated will call system as claimed in claim 14, wherein each storage location comprises slot members attached to a base, defining pie-shaped slots.

16. An automated will call system as claimed in claim 15, wherein each cabinet further comprises a front panel having an opening therethrough, and wherein each opening in each front panel is shaped to permit access to a single slot on each stacked row at one time.

17. An automated will call system as claimed in claim 16, wherein each slot member is releasably attached to the base, forming adjustable slots.

18. An automated will call system as claimed in claim 7, wherein:

a shaft is attached to a central axis of each carousel; and the drive means of each cabinet is attached to the shaft or the corresponding cabinet, such that the controller signals each drive means to rotate the corresponding carousel.

19. An automated will call system as claimed in claim 1, wherein at least one cabinet further comprises a bulk area for the storage of items too large to fit into the storage locations.

20. An automated will call system as claimed in claim 9, wherein:

each light source and each photo-detector are attached to each front panel adjacent each front panel opening; and each reflector is attached to a storage location.

21. An automated will call system as claimed in claim 1, at least one cabinet further comprising a safety sensor.

22. An automated will call system as claimed in claim 21, wherein each safety sensor comprises a light source, reflecting means and a photo-detector.

23. An automated will call system as claimed in claim 1, wherein one cabinet of the plurality of cabinets in communication with the controller is a master and the remaining cabinets are auxiliaries.

24. An automated will call system as claimed in claim 1, wherein the user work station includes:

a keyboard and monitor for input and output of data;

a magnetic strip reader for input of identification data; and a printer.

25. An automated will call system as claimed in claim 1, wherein the controller is free standing.

26. An automated will call system as claimed in claim 1, wherein the controller is embedded within one of the plurality of the cabinets.

27. An automated will call system comprising:

a) an input source for providing identification information;

b) a controller for management of storage and removal of items within the automated will call system, the controller receiving identification information from the input source and in response thereto generating a signal representative of a location of an associated item for tracking said item within the will call system;

c) a plurality of cabinets for the storage of items, each cabinet comprising an interface with the controller, a plurality of storage locations, and at least one interface button; wherein each cabinet further comprises a front panel having a least one opening therethrough dimensioned to permit access to a selected number of storage locations at one time, each front panel having a front face and a rear face;

d) at least one article sensor for each cabinet comprising a light source, reflector and photo-detector, each photo-detector being attached to the rear face of the front panel, each reflector being attached to a rear portion of the storage location such that the light source, reflector and photo-detector are arranged to reflect light energy from the source to the photo-detector along a path through and interior of at least one storage location, each article sensor being in communication with the controller for monitoring the beam of light and providing absolute confirmation of insertion of an item into or removal of an item from a storage location in response to light reflected by the reflector and detected by the photo-detector; and e) a user work station comprising an interface with the controller.

28. An automated will call system as claimed in claim 27, wherein:

the input source is any one of the group comprising: a bar code reader, user work station, and host computer system; and the signal activates at least one indicator,
said indicator being a visible indicator or an audible indicator, wherein the visible indicator comprises at least one indicator light.

29. An automated will call system as claimed in claim 28, wherein the automated will call system further comprises:
a refrigerator comprising at least one indicator light and a controller interface button; and
a secure storage unit comprising locking means, at least one indicator light and a controller interface button.

30. An automated will call system as claimed in claim 27, each cabinet further including a drive means, wherein:
the plurality of storage locations for each cabinet are located on a carousel; and
a shaft is attached to a central axis of each carousel,
each drive means being attached to the shaft of the corresponding cabinet, such that the controller signals each drive means to rotate the corresponding carousel.

31. An automated will call system as claimed in claim 30, the carousel further comprising a row of storage locations circumferentially offset about a vertical shaft and a plurality of vertically stacked rows of storage locations.

32. An automated will call system as claimed in claim 31, wherein:
each storage location comprises slot members releasably attached to a base, defining adjustable pie-shaped slots; and
openings in a front panel are shaped to permit access to a single slot on each stacked row at one time.

33. An automated will call system as claimed in claim 27, wherein:
at least one cabinet further comprises a bulk area for the storage of items too large to fit into the storage locations.

34. An automated will call system as claimed in claim 27, further comprising a safety sensor comprising a light source, reflecting means and photo-detector.

35. An automated will call system as claimed in claim 27, wherein one of the plurality of cabinets in communication with the controller is a master and the remaining cabinets are auxiliaries and wherein the user work station includes:
a keyboard and monitor for input and output of data;
a magnetic strip reader for input of identification data; and
a printer.

36. A method of managing the storage and retrieval of items in an automated will call system comprising:
diffusing light throughout an interior of at least one storage location,
detecting reflection of the diffused light within the at least one storage location,
generating a signal representative of a measure of the detected reflection of the diffused light,
monitoring the generated signal and determining therefrom an item's insertion into or removal from a unique storage location;
receiving identification data associated with an item and storing the data in a memory;
receiving an item having unique identifying indicia thereon for storage in the system;
sensing the identifying indicia on the item prior to accepting the item for storage;
correlating the identification data with the identifying indicia and assigning a unique storage location within the system for receiving the item;
maintaining the unique storage location in memory; and
clearing the unique storage location associated with a removed item from the memory when the item is removed.

37. The method of managing the storage and retrieval of items of claim 36 further comprising:
transmitting instructions from a controller to a storage location in response to assigning a unique location; and
activating a work flow coordinator, illuminating at least one light on the storage location.

38. The method of managing the storage and retrieval of items of claim 37, the monitoring the generated signal and determining therefrom an item's insertion further comprising:
generating a signal indicating insertion of the item into the storage location;
sending the signal indicating insertion to the controller;
receiving the signal indicating insertion at the controller; and
deactivating the work flow coordinator, terminating illumination of said at least one light.

39. The method of managing the storage and retrieval of items of claim 37, the monitoring the generated signal and determining therefrom an item's removal further comprising:
generating a signal representative of the item being removed from the storage location;
sending the signal, indicating removal of the item to the controller;
receiving the signal indicating removal of the item controller confirming retrieval of the item; and
deactivating the work flow coordinator.

* * * * *

UNITED STATES PATENT AND TRADEMARK OFFICE
CERTIFICATE OF CORRECTION

PATENT NO.    : 6,874,684 B1
DATED         : April 5, 2005
INVENTOR(S)   : Denenberg et al.

It is certified that error appears in the above-identified patent and that said Letters Patent is hereby corrected as shown below:

Title page,
Item [57], ABSTRACT,
Line 3, delete "information" and insert -- informational --.

Column 5,
Line 4, delete "in", second occurrence.

Column 7,
Line 53, delete "FIG." and insert -- FIGS. --.

Column 11,
Line 63, delete "-".

Column 12,
Line 37, delete "FIG." and insert -- FIGS. --.

Column 15,
Line 20, delete "FIG." and insert -- FIGS. --.

Column 22,
Line 54, delete "and" and insert -- an --.

Column 24,
Line 44, after "item" insert -- at the --.

Signed and Sealed this

Fourteenth Day of February, 2006

JON W. DUDAS
*Director of the United States Patent and Trademark Office*